United States Patent
Hean et al.

(10) Patent No.: US 11,534,499 B2
(45) Date of Patent: Dec. 27, 2022

(54) EXOSOMES COMPRISING THERAPEUTIC POLYPEPTIDES

(71) Applicants: Evox Therapeutics Ltd., Oxford (GB); Oxford University Innovation Limited, Oxford (GB)

(72) Inventors: Justin Hean, Oxford (GB); Imre Mager, Oxford (GB); Matthew Wood, Oxford (GB); Samir El Andaloussi, Huddinge (SE); Oscar Wiklander, Solna (SE); Joel Nordin, Stockholm (SE)

(73) Assignees: Evox Therapeutics Ltd., Oxfordshire (GB); Oxford University Innovation Limited, Botley (GB)

( * ) Notice: Subject to any disclaimer, the term of this patent is extended or adjusted under 35 U.S.C. 154(b) by 0 days.

(21) Appl. No.: 16/304,580

(22) PCT Filed: May 25, 2017

(86) PCT No.: PCT/GB2017/051479
§ 371 (c)(1),
(2) Date: Nov. 26, 2018

(87) PCT Pub. No.: WO2017/203260
PCT Pub. Date: Nov. 30, 2017

(65) Prior Publication Data
US 2019/0167810 A1 Jun. 6, 2019

(30) Foreign Application Priority Data
May 25, 2016 (GB) .................................. 1609216

(51) Int. Cl.
*A61K 48/00* (2006.01)
*A61K 47/65* (2017.01)
*A61K 41/00* (2020.01)
*A61K 47/64* (2017.01)
*A61K 47/00* (2006.01)
*A61K 9/127* (2006.01)

(52) U.S. Cl.
CPC .......... *A61K 48/0008* (2013.01); *A61K 9/127* (2013.01); *A61K 41/0042* (2013.01); *A61K 47/00* (2013.01); *A61K 47/6425* (2017.08); *A61K 47/65* (2017.08); *A61K 48/005* (2013.01); *A61K 48/0091* (2013.01)

(58) Field of Classification Search
CPC .... A61K 47/00; A61K 9/127; A61K 48/0008; A61K 48/0091; A61K 47/65; A61K 41/0042; A61K 48/005; A61K 47/6425
See application file for complete search history.

(56) References Cited

U.S. PATENT DOCUMENTS

| 5,834,247 | A | 11/1998 | Comb et al. |
| 5,935,822 | A | 8/1999 | Staehelin et al. |
| 8,455,444 | B2 | 6/2013 | Nishimura et al. |

FOREIGN PATENT DOCUMENTS

| CN | 103205435 A | 7/2013 |
| EP | 2127640 A1 | 12/2009 |
| RU | 2010110545 | 9/2011 |
| RU | 2487886 | 7/2013 |
| WO | WO 02/096467 A2 | 12/2002 |
| WO | WO 2013/084000 A2 | 6/2013 |
| WO | WO 2014/168548 A2 | 10/2014 |
| WO | WO 2015/002956 A1 | 1/2015 |
| WO | WO 2015/120548 A1 | 8/2015 |
| WO | WO 2015/138878 A1 | 9/2015 |
| WO | WO 2016/077639 A2 | 5/2016 |
| WO | WO 2016/178532 A1 | 11/2016 |
| WO | WO 2017/203260 A1 | 11/2017 |

OTHER PUBLICATIONS

Mura et al, Stimuli-responsive nanocarriers for drug delivery, Nature Materials, 2013, 12, pp. 991-1003.*
Fong et al, The potential role of self-cleaving purification tags in commercial-scale processes, Trends in Biotechnology, 2010, 28, pp. 272-279.*
Haney et al, Exosomes as drug delivery vehicles for Parkinson's disease therapy, Journal of Controlled Release, 2015, 207, pp. 18-30.*
Machine translation of WO 2016178532 A1, pp. 1-33, accessed Feb. 4, 2021.*
Dinca et al., "Intracellular Delivery of Proteins with Cell-Penetrating Peptides for Therapeutic Uses in Human Disease", International Journal of Molecular Sciences, 2016, vol. 17, No. 263, 13 pages.
El Andaloussi, S. et al. "Exosomes for targeted siRNA delivery across biological barriers", Advanced Drug Delivery Reviews, 2013, vol. 65, No. 3, p. 391-397.
Yu et al., "Therapeutic bispecific antibodies cross the blood-brain barrier in nonhuman primates", Science Translational Medicine, 2014, vol. 6, Issue 261, 11 pages.
Li et al. "Design of linker peptides and its application in fusion protein", Journal of Food and Biotech, vol. 34, No. 11, p. 1121-1127. (Abstract attached), Abstract only.
Wu et al. "The application of intein in the research of membrane protein", Chemistry of Life, 2015, vol. 35, No. 2, p. 200-205. (Abstract attached), Abstract only.

(Continued)

*Primary Examiner* — Li N Komatsu
(74) *Attorney, Agent, or Firm* — Cooley LLP; Matthew Pavao; Gesa Junge

(57) ABSTRACT

The present invention pertains to an inventive release mechanism for extracellular vesicle (EV)-mediated intracellular and intramembrane delivery of therapeutic polypeptides. More specifically, the invention relates to EVs comprising polypeptide constructs which comprise a therapeutic polypeptide releasably attached to an exosomal polypeptide. Furthermore, the present invention pertains to manufacturing methods, pharmaceutical compositions, medical uses and applications, and various other embodiments related to the inventive EVs.

12 Claims, 14 Drawing Sheets
Specification includes a Sequence Listing.

(56) References Cited

OTHER PUBLICATIONS

Topilina et al. "Recent advances in in vivo applications of intein-mediated protein splicing" Mobile DNA, 2014, vol. 5, No. 5, 14 pages.
Mathivanan S. et al. "ExoCarta 2012: database of exosomal proteins, RNA and lipids", Nucleic Acids Research, 2012, vol. 40, p. D1241-D1244.
Villaroya-Beltri et al. "Sorting it out: Regulation of Exosome Loading", Semin Cancer Biol., 2014, vol. 28, p. 3-13.
Wood et al. "A genetic system yields self-cleaving inteins for bioseparations", Nature Biotechnology, 1999, vol. 17, p. 889-892.

* cited by examiner

SEQUENCE LISTING

```
<160> NUMBER OF SEQ ID NOS: 2

<210> SEQ ID NO 1
<211> LENGTH: 5
<212> TYPE: PRT
<213> ORGANISM: Mycobacterium tuberculosis

<400> SEQUENCE: 1

Val Val Val His Asn
1               5
```

-continued

```
<210> SEQ ID NO 2
<211> LENGTH: 6
<212> TYPE: PRT
<213> ORGANISM: Mycobacterium tuberculosis

<400> SEQUENCE: 2

Val Val Val His Asn Cys
1               5
```

EXOSOMES COMPRISING THERAPEUTIC POLYPEPTIDES

RELATED APPLICATIONS

This application is a U.S. National Phase application, filed under 35 U.S.C. § 371, of International Application No. PCT/GB2017/051479, filed on May 25, 2017, which claims priority and the benefit of GB 1609216.5, filed on May 25, 2016, the entire contents of each of which are incorporated herein by reference.

INCORPORATION-BY-REFERENCE OF SEQUENCE LISTING

The contents of the text file name "EVOX-002_NO1US_Seq_Listing_ST25.txt," which was created on Apr. 24, 2020 and is 1 KB in size, are hereby incorporated by reference in their entirety.

TECHNICAL FIELD

The present invention pertains to extracellular vesicle (EV) therapeutics, wherein the EVs comprise at least one polypeptide of interest (PoI).

BACKGROUND TO THE INVENTION

The exquisite specificity between an antibody and its antigen, or for that matter between any type of protein-based biopharmaceutical and its target, is an ideal basis for therapeutic intervention. However, the therapeutic use of antibodies and protein biologics is limited to extracellular targets because of the highly restricted access of large molecular species to the intracellular environment. Various vehicles are under investigation for the delivery of therapeutic polypeptides to the cell interior and recent research has shown the utility of e.g. cell-penetrating peptides (reviewed for instance by Dinca et al., Int J Mol Sci, 2016) and bispecific antibodies which target existing transport pathways (Yu et al., Sci Trans Med, 2014).

A completely different approach was taken in the seminal patent application WO2013/084000, which discloses the use of exosomes for intracellular delivery of biotherapeutics. More specifically, WO2013/084000 discloses how polypeptide-based therapeutics may be loaded into exosomes both via exogenous and endogenous loading techniques. Exogenous loading of exosomes may be carried out using electroporation or transfection of the polypeptide of interest into exosomes post-isolation from the parental cell, whereas endogenous loading is based on transfection of the parental cell with a construct encoding the polypeptide of interest, followed by overexpression of the construct and harvesting of exosomes comprising the biotherapeutic polypeptide.

Another groundbreaking patent application (WO2014/168548) discloses therapeutic delivery vesicles, such as exosomes, having attached to their membrane a polypeptide construct comprising at least one carrier polypeptide fused to at least one therapeutic polypeptide, which is present at least partially on the outside of the vesicle, so that it is displayed to the extravesicular environment. Other patent applications have attempted to use exosomes for the delivery of protein biologics, such as, in the case of WO2015/138878, heparin-binding epidermal growth factor (HB-EGF).

However, successful intracellular delivery of bioactive protein biologics, especially antibodies/intrabodies and other polypeptides intended to interact with a specific intracellular target, often necessitates that the therapeutic polypeptide of interest is delivered with high efficacy in its free and unconjugated form. The exogenous loading of exosomes post isolation is often a cumbersome and ineffective strategy for loading of polypeptides, and similarly the endogenous loading strategies of the prior art implies that intraluminal EV loading is either inefficient or that the polypeptide of interest (PoI) is not present in its bioactive unconjugated form. Recently, WO2016/178532 described an optogenetic method for creating protein-carrying EVs, wherein two complex dimeric optogenetic constructs are introduced into a parental cell. Upon exogenously applied light exposure, two different optogenetic proteins associate and upon ceased light exposure the proteins dissociate. This method requires extended long-term exposure of biological material to a light source in order to transport the protein into exosomes and subsequently to release it from its exosomal transporter. As a result, the method suffers from problems with scalability, potential toxicity issues, and is also highly cumbersome to carry out, in part due to the long-term exogenous application of light. Furthermore, the dimeric construct means that there is a need for multiple vectors and that the risk of protein misfolding, toxic protein aggregation, and translational errors increases substantially, in addition to the risk of imperfect association and dissociation between the proteins.

SUMMARY OF THE INVENTION

It is hence an object of the present invention to overcome the above-identified problems associated with the delivery of protein biologics into a target cell, and to satisfy the existing needs within the art, for instance to enable reaching intracellular targets with antibodies or intrabodies, enzymes for enzyme replacement therapy, or gene editing enzymes, or any other type of polypeptide that is intended to have a bioactive effect in a target cell or target tissue. The present invention achieves this by utilizing extracellular vesicle (EV)-based therapeutics, which are based on exosomes or any other type of EVs comprising at least one polypeptide/protein of interest (PoI), wherein the PoI is released from an endogenously activatable polypeptide-based release system and subsequently delivered into a target cell, e.g. specifically into a suitable cellular compartment or into an organelle of a target cell. The release system of the present invention is based on a fusion protein between an exosomal polypeptide and a domain that enables endogenously activatable releasable attachment of the PoI, meaning that the PoI may be released through an endogenous activation trigger into one of more of e.g. the lumen of an EV, into the membrane of an EV, or into any compartment or organelle of a target cell or target tissue. Importantly, endogenous activation of the polypeptide-based release domain means that the method is highly scalable, contains no extra steps during which biological material is exposed for extended time periods to potentially toxic exogenous stimuli or conditions, and is transferable across therapeutics platforms. Without wishing to be bound by any theory, it is surmised that the endogenous activation may be a result of e.g. a drop in pH, competition for binding partners, and generally any change of cell biological conditions which may be conducive to triggering release of the PoI through activation of the polypeptide-based release domain.

This highly sophisticated approach to the delivery of unconjugated therapeutic polypeptides of interest into the lumen or the membrane of an EV enables extremely efficient delivery of bioactive polypeptides of therapeutic interest into the intracellular environment and/or to any type of cellular membrane structure (such as the plasma membrane, the membrane of an organelle such as the nucleus, a lysosome or the endoplasmic reticulum (ER) or any other type of membrane compartment) of a target cell. The present invention may thus be applied to any type of intracellular and/or intramembrane delivery of polypeptides, for instance for the introduction or replacement of any type of protein or peptide. A non-limiting example may be an enzyme that is absent or inactive in diseases involving e.g. a genetic abnormality, such as lysosomal storage diseases, or any type of intracellular or integral membrane protein that needs to be replaced or be present in a higher concentration in a target. As a further non-limiting example, the present invention is highly useful in the treatment of cancer, wherein the EVs of the present invention may be utilized to introduce into the intracellular environment a tumor suppressor protein (or a variant or derivative thereof) such as p53 or p21 or any type of polypeptide (such as an intrabody or an antibody) that binds to and inhibits a tumorigenic pathway. Yet other non-limiting examples include to deliver transcription factors or components of signaling pathways for modulating inflammatory responses or induce tissue repair, or to deliver RNA-binding proteins which may carry with them single or double RNA strands which may themselves confer therapeutic activity.

The present invention thus pertains inter alia to EVs comprising at least one PoI, wherein the at least one PoI is attached to an exosomal polypeptide via an endogenously activatable release system. For clarity, the present invention thus relates to both EVs comprising a PoI which has been released into the lumen of an EV and/or into the membrane of an EV by a release system, and EVs comprising a PoI which is still attached in a releasable manner to an endogenously activatable polypeptide-based release system. The modularity of the polypeptide constructs of the present invention (which comprises a polypeptide of interest, a polypeptide-based endogenously activatable release domain, and an exosomal polypeptide) enables a highly controllable endogenous production of EVs for the delivery of unconjugated PoIs (as above-mentioned either as a soluble PoI or as a membrane-associated PoI, wherein the PoI may face either the external environment or the internal environment or both in a transmembrane fashion). This is in complete contrast to the prior art, which merely describes endogenous loading of PoIs which are either permanently conjugated to exosomal proteins or PoIs loaded into EVs without the aid of any exosomal polypeptide, or PoIs which are transported and released into EVs as a result of extended long-term exposure to an exogenous light source, which means that the loading and the production processes are extremely inefficient, cumbersome, un-scalable and/or potentially toxic in comparison to loading and EV production as per the present invention.

Furthermore, the present invention pertains to several novel methods for loading and production of EVs comprising PoIs, cells comprising polynucleotide and/or polypeptide constructs enabling such production, and inventive polynucleotide and/or polypeptide constructs as such. More in detail, the present invention relates to the use of cis-cleaving polypeptides (i.e. polypeptides or peptides comprising specific sequences of amino acids that trigger release (which can take place by a variety of mechanisms, e.g. splicing or cleavage) of desired parts of the peptide to in turn release the PoI) and nuclear localization signal (NLS)-binding polypeptides (NLSBPs) (e.g. an importin alpha polypeptide) for EV-mediated delivery of intraluminal and/or membrane-associated unconjugated polypeptides of interest (PoIs). In one separate embodiment, the present inventors have contemplated the use of a simple monomeric polypeptide-based release system which can be triggered by a very rapid light boost (as opposed to extended light exposure-based transport and release systems such as in WO2016/178532).

The present invention further pertains to methods for intracellular delivery of unconjugated PoIs, wherein such methods comprise the steps of contacting a target cell with an EV comprising (i) a PoI releasably attached to an exosomal polypeptide via endogenously triggered release domain(s) or (ii) a PoI released via endogenous activation from an exosomal polypeptide (normally inside the lumen or the membrane of the EV). The EV may typically enter the target cell and deliver its polypeptide cargo, resulting in highly efficient intracellular or intramembrane delivery of the therapeutic polypeptide. The EVs and the methods for their production and for intracellular delivery thus have extensive medical potential, for instance in the prophylaxis and/or treatment of a large number of diseases and ailments, notably within oncology, inflammation and autoimmunity, neuroinflammatory and neurodegenerative disorders, genetic diseases, lysosomal storage disorders, organ injuries and failure, muscular dystrophies such as DMD, cardiovascular and metabolic disorders, kidney and liver diseases such as non-alcoholic steatohepatitis (NASH), etc.

DETAILED DESCRIPTION OF THE INVENTION

Figure 1:
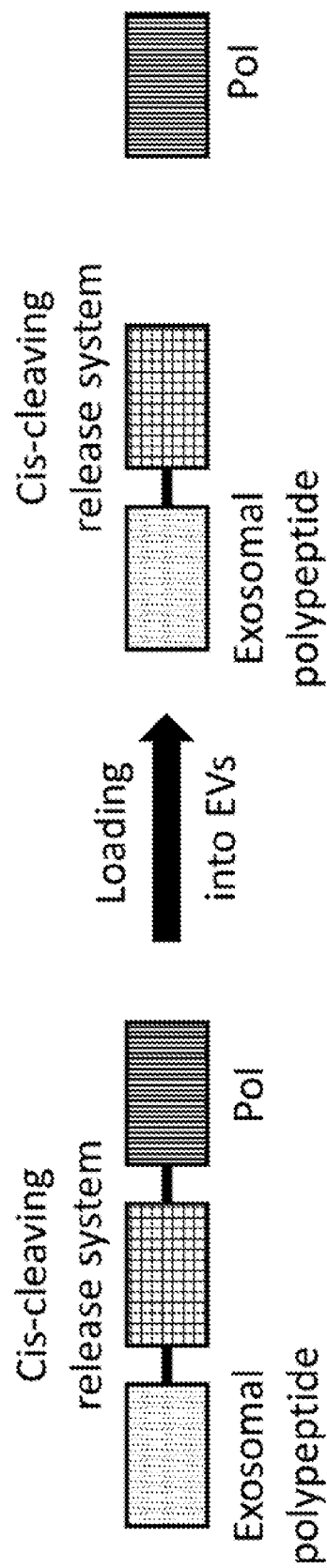
FIG. 1 shows a schematic illustration of a polypeptide construct comprising a cis-cleaving release system (such as an intein) for release of a polypeptide of interest (PoI).
Figure 2:
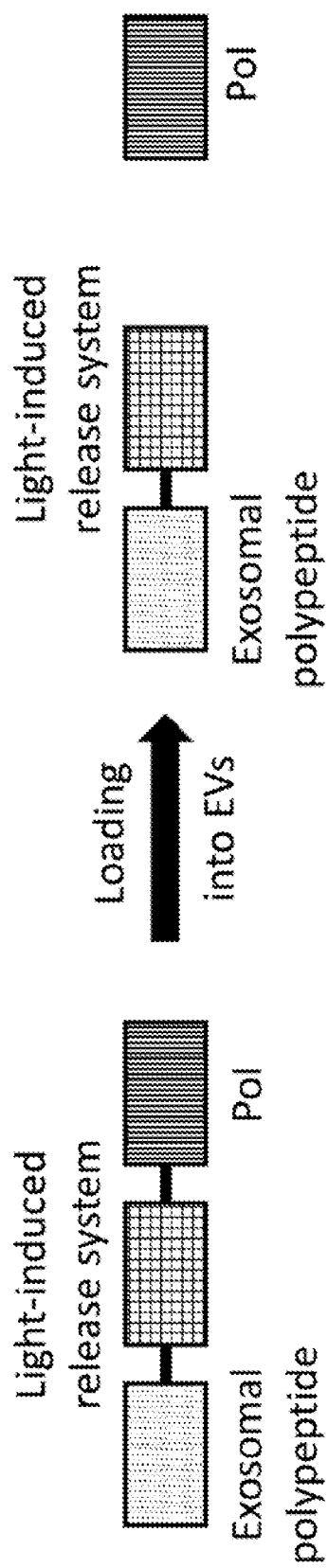
FIG. 2 shows a general illustration of a polypeptide construct comprising a monomeric short-term light-induced cleavage release system for release of a PoI. A short-term light boost leads to cleavage of the release system and thereby release of the PoI, without any toxic effects and without issues with scalability.

The present invention pertains to EVs comprising a polypeptide construct, which in turn comprises (i) at least one PoI, (ii) at least one exosomal polypeptide, and (iii) at least one polypeptide-based release system, wherein the at least one PoI is releasably attached to the at least one exosomal polypeptide with the aid of the release system, wherein the release system is endogenously activatable and the release of the PoI is thus triggered automatically without being dependeint on any exogenous stimuli. Further, the present invention also relates to EVs comprising at least one PoI which has been released from the at least one exosomal polypeptide with the aid of the release system in the EV, either essentially in the lumen of the EV or in association (e.g. into) with the EV membrane. Furthermore, the invention relates to various related aspects as will be described in greater detail below, for instance polynucleotide and polypeptide constructs and cells comprising such constructs, production methods and methods for intracellular delivery of polypeptides/proteins of interest in vitro and in vivo, as well as medical applications of such EVs and pharmaceutical compositions containing such EVs.

For convenience and clarity, certain terms employed herein are collected and described below. Unless otherwise defined, all technical and scientific terms used herein have the same meaning as commonly understood by one of ordinary skill in the art to which this invention belongs.

Where features, aspects, embodiments, or alternatives of the present invention are described in terms of Markush groups, a person skilled in the art will recognize that the invention is also thereby described in terms of any individual member or subgroup of members of the Markush group. The person skilled in the art will further recognize that the invention is also thereby described in terms of any combination of individual members or subgroups of members of Markush groups. Additionally, it should be noted that embodiments and features described in connection with one of the aspects and/or embodiments of the present invention also apply mutatis mutandis to all the other aspects and/or embodiments of the invention. For example, the various at least one polypeptides of interest (PoI) described in connection with the EVs is to be understood to be disclosed and relevant also in the context of the polypeptide constructs or in the context of the pharmaceutical compositions comprising EVs, or as expression products of the polynucleotide constructs as per the present invention. Furthermore, certain embodiments described in connection with certain aspects, for instance the administration routes of the EVs, as described in relation to aspects pertaining to treating certain medical indications, may naturally also be relevant in connection with other aspects and/or embodiment such as aspects/embodiments pertaining to the pharmaceutical compositions or the intracellular delivery methods of the present invention. As a general remark, the polypeptides of interest (PoI), the exosomal polypeptides, the endogenously activatable release systems, and the targeting moieties, the cell sources, and all other aspects, embodiments, and alternatives in accordance with the present invention may be freely combined in any and all possible combinations without deviating from the scope and the gist of the invention. Furthermore, any polypeptide or polynucleotide or any polypeptide or polynucleotide sequences (amino acid sequences or nucleotide sequences, respectively) of the present invention may deviate considerably from the original polypeptides, polynucleotides and sequences as long as any given molecule retains the ability to carry out the technical effect associated therewith. As long as their biological properties are retained the polypeptide and/or polynucleotide sequences according to the present application may deviate with as much as 50% (calculated using for instance BLAST or ClustalW) as compared to the native sequence, although a sequence identity that is as high as possible is preferable. The combination (fusion) of e.g. at least one polypeptide of interest and at least one peptide/polypeptide-based release system and at least one exosomal polypeptide implies that certain segments of the respective polypeptides may be replaced and/or modified, meaning that the deviation from the native sequence may be considerable as long as the key properties are conserved. Similar reasoning thus naturally applies to the polynucleotide sequences encoding for such polypeptides.

The terms "extracellular vesicle" or "EV" or "exosome" shall be understood to relate to any type of vesicle that is, for instance, obtainable from a cell, for instance a microvesicle (e.g. any vesicle shed from the plasma membrane of a cell), an exosome (e.g. any vesicle derived from the endo-lysosomal pathway), an apoptotic body (e.g. obtainable from apoptotic cells), a microparticle (which may be derived from e.g. platelets), an ectosome (derivable from e.g. neutrophils and monocytes in serum), prostatosome (e.g. obtainable from prostate cancer cells), or a cardiosome (e.g. derivable from cardiac cells), etc. Furthermore, the said terms shall also be understood to relate to lipoprotein particles, such as LDL, VLDL, HDL and chylomicrons, as well as extracellular vesicle mimics, cellular membrane vesicles obtained through membrane extrusion or other techniques, etc. Essentially, the present invention may relate to any type of lipid-based structure (with vesicular morphology or with any other type of suitable morphology) that can act as a delivery or transport vehicle for the polypeptide of interest (PoI) and polypeptide constructs containing such PoIs. It will be clear to the skilled artisan that when describing medical and scientific uses and applications of the EVs, the present invention normally relates to a plurality of EVs, i.e. a population of EVs which may comprise thousands, millions, billions, trillions or even quadrillions or quintillions (e.g. $10^3$-$10^{18}$) of EVs, or even greater populations of EVs ($>10^{18}$ of EV particles). In the same vein, the term "population", which may e.g. relate to an EV comprising a certain type of PoI and/or a certain type of polypeptide construct comprising a PoI, shall be understood to encompass a plurality of entities (typically counted as particles) constituting such a population. In other words, individual EVs when present in a plurality constitute an EV population. Thus, naturally, the present invention pertains both to individual EVs comprising various PoIs and populations comprising EVs which in turn comprise various PoIs, as will be clear to the skilled person.

The terms "exosomal polypeptide" and "exosomal protein" and "EV polypeptide" and "EV protein" are used interchangeably herein and shall be understood to relate to any polypeptide that can be utilized to transport a polypeptide construct (which typically comprises, in addition to the exosomal protein, at least one polypeptide of interest and at least one polypeptide-based release system) to a suitable vesicular structure, i.e. to a suitable EV. More specifically, the term "exosomal polypeptide" shall be understood as comprising any polypeptide that enables transporting, trafficking or shuttling of a polypeptide construct (which as abovementioned typically comprises at least one PoI and at least one polypeptide based release system, but which may also include a targeting peptide/polypeptide) to a vesicular structure, such as an exosome. Examples of such exosomal polypeptides are for instance CD9, CD53, CD63, CD81, CD54, CD50, FLOT1, FLOT2, CD49d, CD71, CD133, CD138, CD235a, ALIX, Syntenin-1, Syntenin-2, Lamp2b, TSPAN8, TSPAN14, CD37, CD82, CD151, CD231, CD102, NOTCH1, NOTCH2, NOTCH3, NOTCH4, DLL1, DLL4, JAG1, JAG2, CD49d/ITGA4, ITGB5, ITGB6, ITGB7, CD11a, CD11b, CD11c, CD18/ITGB2, CD41, CD49b, CD49c, CD49e, CD51, CD61, CD104, Fc receptors, interleukin receptors, immunoglobulins, MHC-I or MHC-II components, CD2, CD3 epsilon, CD3 zeta, CD13, CD18, CD19, CD30, CD34, CD36, CD40, CD40L, CD44, CD45, CD45RA, CD47, CD86, CD110, CD111, CD115, CD117, CD125, CD135, CD184, CD200, CD279, CD273, CD274, CD362, COL6A1, AGRN, EGFR, GAPDH, GLUR2, GLUR3, HLA-DM, HSPG2, L1CAM, LAMB1, LAMC1, LFA-1, LGALS3BP, Mac-1 alpha, Mac-1 beta, MFGE8, SLIT2, STX3, TCRA, TCRB, TCRD, TCRG, VTI1A, VTI1B, and any combinations thereof, but numerous other polypeptides capable of transporting a polypeptide construct to an EV are comprised within the scope of the present invention. The EV proteins are typically of human origin and can be found in various publicly available databases such as Uniprot, RCSB, etc.

The terms "polypeptide of interest", "protein of interest", "therapeutic polypeptide of interest", "PoI", "biotherapeutic", "biologic", and "protein biologic" are used interchangeably herein and shall be understood to relate to any polypeptide that can be utilized for therapeutic purposes through e.g. binding a target and/or in any other way interacting with an interaction partner and/or replace a protein and/or supplement or complement an existing intracellular protein, thereby exerting its therapeutic effect. Said terms may represent the following non-limiting examples of therapeutic polypeptides of interest: antibodies, intrabodies, single chain variable fragments (scFv), affibodies, bi-och multispecific antibodies or binders, receptors, ligands, enzymes for e.g. enzyme replacement therapy or gene editing, tumor suppressors, viral or bacterial inhibitors, cell component proteins, DNA and/or RNA binding proteins, DNA repair inhibitors, nucleases, proteinases, integrases, transcription factors, growth factors, apoptosis inhibitors and inducers, toxins (for instance *pseudomonas* exotoxins), structural proteins, neurotrophic factors such as NT3/4, brain-derived neurotrophic factor (BDNF) and nerve growth factor (NGF) and its individual subunits such as the 2.5S beta subunit, ion channels, membrane transporters, proteostasis factors, proteins involved in cellular signaling, translation- and transcription related proteins, nucleotide binding proteins, protein binding proteins, lipid binding proteins, glycosaminoglycans (GAGs) and GAG-binding proteins, metabolic proteins, cellular stress regulating proteins, inflammation and immune system regulating proteins, mitochondrial proteins, and heat shock proteins, etc. In one preferred embodiment, the PoI is a CRISPR-associated (Cas) polypeptide with intact nuclease activity which is associated with (i.e. carries with it) an RNA strand that enables the Cas polypeptide to carry out its nuclease activity in a target cell once delivered by the EV. Alternatively, in another preferred embodiment, the Cas polypeptide may be catalytically inactive, to enable targeted genetic engineering. Yet another alternative may be any other type of CRISPR effector such as the single RNA-guided endonuclease Cpf1. The inclusion of Cpf1 as the PoI is a particular preferred embodiment of the present invention, as it cleaves target DNA via a staggered double-stranded break, Cpf1 may be obtained from species such as Acidaminococcus or Lachnospiraceae. In yet another exemplary embodiment, the Cas polypeptide may also be fused to a transcriptional activator (such as the P3330 core protein), to specifically induce gene expression. Additional preferred embodiments include PoIs selected from the group comprising enzymes for lysosomal storage disorders, for instance glucocerebrosidases such as imiglucerase, alpha-galactosidase, alpha-L-iduronidase, iduronate-2-sulfatase and idursulfase, arylsulfatase, galsulfase, acid-alpha glucosidase, sphingomyelinase, galactocerebrosidase, galactosylceramidase, ceramidase, alpha-N- acetylgalactosaminidase, beta-galactosidase, lysosomal acid lipase, acid sphingomyelinase, NPC1, NPC2, heparan sulfamidase, N-acetylglucosaminidase, heparan-α-glucosaminide-N-acetyltransferase, N-acetylglucosamine 6-sulfatase, galactose-6-sulfate sulfatase, galactose-6-sulfate sulfatase, hyaluronidase, alpha-N-acetyl neuraminidase, GlcNAc phosphotransferase, mucolipin1, palm itoyl-protein thioesterase, tripeptidyl peptidase I, palmitoyl-protein thioesterase 1, tripeptidyl peptidase 1, battenin, linclin, alpha-D-mannosidase, beta-mannosidase, aspartylglucosaminidase, alpha-L-fucosidase, cystinosin, cathepsin K, sialin, LAMP2, and hexoaminidase. In other preferred embodiments, the PoI may be e.g. an intracellular protein that modifies inflammatory responses, for instance epigenetic proteins such as methylases and bromodomains, or an intracellular protein that modifies muscle function, e.g. transcription factors such as MyoD or Myf5, proteins regulating muscle contractility e.g. myosin, actin, calcium/binding proteins such as troponin, or structural proteins such as Dystrophin, utrophin, titin, nebulin, dystrophin-associated proteins such as dystrobrevin, syntrophin, syncoilin, desmin, sarcoglycan, dystroglycan, sarcospan, agrin, and/or fukutin. The PoIs are typically proteins or peptides of human origin unless indicated otherwise by their name, any other nomenclature, or as known to a person skilled in the art, and they can be found in various publicly available databases such as Uniprot, RCSB, etc.

The term "released inside" as in the context of "released inside an EV" or "released inside a target cell" can be understood to mean release of a polypeptide of interest (PoI) completely and/or partially inside the EV (or the target cell), i.e. that a PoI is released into the lumen of an EV (or the target cell), into the membrane of an EV (or the target cell) either completely or partially (e.g. into a transmembrane configuration) or onto the outside of the EV (or the target cell) membrane. Said term may also be understood to mean release of a PoI onto the external side of the EV membrane (or the target cell). Furthermore, it may also include being released inside any biological system, e.g. a particular tissue or a target organ.

The terms "endogenous activation", "endogenous triggering" and variants thereof (such as "endogenously activatable" or "endogenously triggered") shall be understood to relate to activation, induction, and/or triggering of release of the PoI by the release system without any exogenous stimuli, i.e. the release of the PoI is triggered inside an EV or inside a cell by the mere action of the surrounding exosomal and/or cellular and/or biological environment (e.g. as a result of changes in pH, changes in other physiological parameters such as salinity, competition between binding partners, enzymatic activity e.g. proteolytic activity, etc.).

The terms "source cell" or "EV source cell" or "parental cell" or "cell source" or "EV-producing cell" or any other similar terminology shall be understood to relate to any type of cell that is capable of producing EVs under suitable cell culturing conditions, for instance in suspension culture or in adherent culture or any in other type of culturing system. The source cells per the present invention may be select from a wide range of cells, for instance mesenchymal stem or stromal cells (obtainable from e.g. bone marrow, adipose tissue, Wharton's jelly, perinatal tissue, tooth buds, umbilical cord blood, etc.), amnion cells, amnion epithelial cells, myeloid suppressor cells, immortalized cell lines of which human embryonic kidney (HEK) cells represent one non-limiting example, dendritic cells (DCs) or other immune system cells such as macrophages, monocytes, B- or T-cells, NK cells, neutrophils, eosinophils, mast cells or basophils, etc. Generally, EVs may be derived from essentially any cell source, be it a primary cell source or an immortalized cell line. The EV source cells may be any embryonic, fetal, and adult somatic stem cell types, including induced pluripotent stem cells (iPSCs) and other stem cells derived by any method. When treating neurological diseases, one may contemplate to utilize as source cells e.g. primary neurons, astrocytes, oligodendrocytes, microglia, and neural progenitor cells. The source cell may be either allogeneic, autologous, or even xenogeneic in nature to the patient to be treated, i.e. the cells may be from the patient himself or from an unrelated, matched or unmatched donor. In certain contexts, allogeneic cells may be preferable from a medical standpoint, as they could provide immuno-modulatory effects that may not be obtainable from autologous cells of a patient suffering from a certain indication. For instance, in the context of treating peripheral or neurological inflammation, allogeneic MSCs may be preferable as EVs obtainable from such cells may enable immuno-modulation via e.g. macrophage and/or neutrophil phenotypic switching (from pro-inflammatory M1 or N1 phenotypes to anti-inflammatory M2 or N2 phenotypes, respectively). Conversely, when utilizing EVs for treating a solid or hematological malignancy, it may be preferable to select immune cells such as DCs as the EV-producing cell source.

In a first aspect, the instant invention relates to an EV comprising at least one polypeptide of interest (PoI), wherein the at least one PoI is releasably attached to an exosomal polypeptide. The attachment of the PoI to the exosomal polypeptide is releasable, in order to enable efficient, non-obstructed loading and endogenously triggered release of the therapeutic polypeptide of interest into the EV. The releasable attachment between the PoI and the exosomal polypeptide is a feature mediated by an inventive release system which enables endogenously activatable release of the PoI inside the EV and/or subsequently inside a target cell or target tissue, to optimize loading and therapeutic activity. The release system is a polypeptide-based system that may be selected from the group comprising various releasable polypeptide interaction systems which may be activated or triggered without the need for exogenous stimuli (i.e. the release systems are typically triggered by endogenous activity within a cell or an EV, or essentially within any biological system), for instance a cis-cleaving polypeptide-based release system (e.g. based on inteins), a nuclear localization signal (NLS)—NLS binding protein (NLSBP)-based release system or release systems based on other protein domains. In one embodiment, a monomeric light-induced cleavage-based release system may be utilized, where only a very short boost of light is utilized to start an endogenous proteolytic cleavage of a monomeric protein domain and release the PoI.

In a preferred embodiment, the present invention relates to an EV comprising a polypeptide of interest which is releasably attached to an intein release system, and/or a polypeptide of interest (PoI) that has been released from an intein release system inside the EV or inside a target cell or target organ. A typical polypeptide construct that employs an intein release system can be described schematically as follows (the below notation is not to be construed as illustrating any C and/or N terminal direction, it is merely meant for illustration purposes):

PoI-Cis-cleaving polypeptide-Exosomal protein

Alternatively, the polypeptide construct may be designed as follows, to include a targeting moiety that will be displayed on the surface of the EV, to even further enhance its therapeutic potential by targeting a tissue or cell type of interest:

PoI-Cis-cleaving polypeptide-Exosomal protein-Targeting Moiety

The cis-cleaving polypeptide-based release system may be either a fast or a slow cleaving release system. In certain instances, one may opt to utilize a fast-cleaving cis-cleaving release system (such as a fast-cleaving cis-cleaving intein), whereas a slow-cleaving release system may be advantageous in other settings. Generally, a slow-cleaving release system may be employed to allow longer time for loading of PoIs into EVs, whereas the fast-cleaving system may be preferable when EVs need to be harvested quickly.

In a preferred embodiment, the cis-cleaving release system is based on an intein system, wherein the C-terminal portion of the intein may comprise the amino acid sequences Val-Val-Val-His-Asn (SEQ ID NO: 1) or Val-Val-Val-His-Asn-Cys (SEQ ID NO: 2). Truncated or in other ways optimized inteins, i.e. inteins where one or more amino acids have been removed or replaced to enhance functionality, may also be used for the purposes of the present invention. Without wishing to be bound by any theory it is surmised that truncation or increased-functionality mutation may increase the pH responsiveness of the intein, which further increases its utility in releasing bioactive PoIs from EV-based delivery system as EV may be internalized into cells via endocytosis processes. However, more broadly, the cis-cleaving release system may be selected from a group of cis-cleaving systems comprising various other polypeptide-based release systems, for instance Sortase A, N-terminus protease, FrpC, and cysteine protease domains, or other suitable cis-cleaving release systems, and any combinations thereof. The cis-cleaving release proteins may advantageously be attached to intraluminal exosomal polypeptide termini, to allow for release of the PoI inside an EV or into an EV membrane, although other points of attachment may also be employed, e.g. integral attachment points.

In one embodiment of the invention, the release of the PoI from the exosomal polypeptide which has guided the PoI to the EV may be achieved by light-induced cleavage. Unlike in the prior art, the present invention employs monomeric light-induced cleavage-based release systems which after a short light boost undergo endogenous activation and which may be selected from the group comprising monomeric proteins such as Kaede, KikGR, EosFP, tdEosFP, mEos2, PSmOrange, and the GFP-like Dendra proteins Dendra and Dendra2. Unlike optogenetic dimerization systems such as CRY2-CIBN, monomeric proteins such as Dendra, Kaede, KikGR, EosFP, tdEosFP, mEos2, PSmOrange and Dendra2 have the advantages of leaving only a small residual polypeptide domain on the PoI, which means that the bioactivity of the delivered PoI is not negatively affected. Furthermore, in contrast to optogenetic dimerization domains, the light-induced cleavage-based release systems are considerably easier to control, meaning that the loading of the PoI into the EV is highly precise. The light-induced cleavage-based released systems of the present invention thus enable highly controllable release of the PoI at desired time points and at desired locations both in vitro and in vivo, simply by exposure to light of suitable wavelengths (in the case of Dendra, Kaede, KikGr and most other light-induced cleavage-based release proteins either UV or blue light, whereas in the case of PSmOrange longer wavelengths in the red-orange spectrum). Importantly, a cleavage-based light-induced release system is merely requiring a very short boost of light in order to effectuate an endogenous process of cleavage, which means that potentially toxic effects of extended and cumbersome light exposure periods can be avoided. Polypeptide constructs based on light-induced cleavage release systems may be described schematically as follows (the below notation is not to be construed as illustrating any C and/or N terminal direction, it is merely meant for illustration purposes):

PoI-Dendra-Exosomal protein
PoI-Kaede-Exosomal protein

At a suitable time during the EV production process the polypeptide construct comprising the PoI, the light-induced cleavage system, and the exosomal polypeptide is exposed to a boost of light of a suitable wavelength, resulting in cleavage and release of the PoI. Upon short-term exposure to UV or blue light, Dendra or other monomeric UV/blue light-responsive light-induced cleavage release proteins, which may be inserted as a fusion between the PoI and the exosomal polypeptide, are cleaved via an internal peptide backbone cleavage, liberating the PoI and the exosomal protein. Small polypeptide domains may remain on both the PoI and the exosomal polypeptide but the activity of the PoI is not hampered by the presence of these small residues.

In yet another embodiment of the present invention, the release system may be based on the interaction between a nuclear localization signal (NLS) binding polypeptide (NLSBP) and an NLS. The NLSBP-NLS release system may comprise at least one PoI comprising at least one classical or non-classical NLS. As a further alternative, NLS-like sequences (NLSLS) can be used that bind to the NLSBP but that do not trigger nuclear import of the NLSLS PoI. The NLS may be a naturally occurring NLSLS or NLS (as would be the case with most PoIs destined for the nucleus, e.g. transcription factors and nucleases) with or without an overlapping RNA/DNA binding domain, or an NLS that is recombinantly fused to a PoI which does not inherently comprise an NLS. The exosomal polypeptide is in turn modified to comprise a suitable NLSBP (for instance from the importin alpha or beta families e.g. the importin alpha KPNA1, or any other proteins involved in nuclear import), resulting in a releasable attachment between the NLS-containing PoI and the NLSPB-containing exosomal polypeptide, upon endogenous activation of the NLS-NLSBP release system. The trigger of the release of the PoI is typically driven by competition between different NLS-NLSBP pairs, which results in release of the PoI. Polypeptide constructs based on the NLS-NLSBP release systems may be described schematically as follows (the below notation is not to be construed as illustrating any C and/or N terminal direction, it is merely meant for illustration purposes):

PoI-NLS-NLSBP-Exosomal protein

As abovementioned, NLSBPs present in the target cell will (upon EV-mediated delivery of the NLS-containing PoI) out-compete the NLSBP-containing exosomal polypeptide, resulting in the PoI being endogenously liberated and trafficked to the correct cellular compartment. Naturally, the NLSBP-NLS-based release system is highly suitable for polypeptides of interest that are meant to exert their desired activity in the nucleus and/or the nucleolus, however proteins of interest destined to cytoplasm or other intracellular compartments are also compatible with the NLS-NLSBP release system, especially when using NLSLS instead of NLS. Non-limiting examples of NLSBP-NLS release systems may comprise the following: KPNA1-NRF2, KPNA6-STAT3, KPNB1-STAT3, KPNA2- and HSF1. NLSBPs may comprise importins from the importin alpha and beta families, and other NLS-binding proteins, including KPNA1, KPNA2, KPNA3, KPNA4, KPNA5, KPNA6, KPNA7, KPNB1, IPO4, IPO5, IPO7, IPO8, IPO9, IPO11, IPO13, TPNO1, TNPO2, TNPO3, HIKESHI, SNUPN, HEATR3, and other RAN binding proteins. NLS-containing proteins may be selected from non-limiting examples such as transcription factors, nucleases and other nuclear proteins such as CREB, C/EBP, bZIP, bHLH, MyoD, cMyc, SERBP, NF-1, Cys4, GATA-factors, OCT4, NANOG, KLF4, SOX2, HSF1, STAT3, SMAD3, p53, MEF2, SRF, NFkB, CAS9, Zinc finger nucleases, hnRNPA1, hnRNPA2, NUP153, RPL23A, RPS7, RPL5, RPL23A, H2A, H2B, H3 and H4 histones, TNRC6A, SRP19, SNAI1, PRKCI, HSP70, U1 snRNP, U2 snRNP, U4 snRNP, U5 snRNP, and U6 snRNP. Generally, non-limiting examples of suitable PoIs are for instance nucleases such as Cas and Cas9 (which is an RNA-guided DNA endonuclease from *Streptococcus pyogenes*, among other bacteria); transcription-related proteins such as NF-κB and NRF2; DNA-binding proteins such as histones and polymerases; RNA-binding proteins such as hnRNPA1-2 and the MS2 coat protein which may be used to transport various types of RNAs; antibodies and/or intrabodies with nuclear targets, enzymes for enzyme replacement therapies such as NPC1, NPC2 and GBA, etc. A preferred example of the present invention is fusing KPNA1 to CD63 and co-expressing with MyoD in a suitable EV source cell, such as an MSC or an amnion epithelial cell, thereby obtaining therapeutic EVs with strong applicability in treating e.g. DMD.

As above-mentioned, the present invention relates to EV-based therapeutics comprising essentially any polypeptide of interest (PoI), typically for therapeutic or prophylactic purposes but potentially also for cosmetic uses. The PoI—or PoIs in the cases where a plurality (i.e more than one) PoI are utilized—may be any suitable polypeptide, that is any molecule comprising a plurality of amino acids, i.e. a protein or a peptide. The PoI may be selected from anyone of the following non-limiting examples of therapeutic, prophylactic, or cosmetic polypeptides: antibodies, intrabodies, single chain variable fragments (scFv), affibodies, bi-och multispecific antibodies or binders, receptors, ligands, enzymes such as enzymes lacking and/or defect in lysosomal storage diseases (LSDs), tumor suppressors such as p53, pVHL, APC, CD95, ST5, YPEL3, ST7, and ST14, viral or bacterial inhibitors, cell component proteins, DNA and/or RNA binding proteins, nucleases such as Cas, Cas9, and Cpf1, proteinases, integrases, transcription factors, growth factors, apoptosis inhibitors and inducers, structural proteins, ion channels, membrane transporters, proteostasis factors, proteins involved in cellular signaling, translation- and transcription related proteins, nucleotide binding proteins, protein binding proteins, lipid binding proteins, glycosaminoglycans (GAGs) and GAG-binding proteins, metabolic proteins, cellular stress regulating proteins, inflammation and immune system regulating proteins, mitochondrial proteins, and heat shock proteins, etc. The fact that EVs enable reaching the intracellular milieu in a highly efficient manner means that a vast number of intracellular targets becomes druggable. Thus, a therapeutic protein of interest (PoI) is typically either a protein that binds to an intracellular target (for instance an intrabody against an oncogenic protein such as c-Myc or a decoy receptor binding its intracellular interaction partner) or a PoI that is meant to exert a desired effect intracellularly (the PoI may for instance be dystrophin as a treatment of Duchenne's muscular dystrophy (DMD), a PoI for replacement of a missing or defect protein (such an enzyme like NPC1, GBA, or AGAL, etc. for enzyme replacement therapy, the Huntingtin protein or BDNF for the treatment of e.g. Huntington's disease or other neurodegenerative disorders), a tumor suppressor such as p53 for treatment of cancer, or an NFkB inhibitor for treatment of inflammatory diseases. Targets of interest for intrabodies delivered with the aid of the EVs of the present invention may include pathological forms of alpha-synuclein, LRRK2, Tau, Beta amyloid, APP, C9orf72, SOD1, TDP43, FUS and prion proteins. One class of PoIs with considerable therapeutic potential are the RNA-binding proteins (RBPs), which may be used to aid intracellular delivery of RNA therapeutics such as mRNA, RNAi agents such as short-hairpin RNA or microRNA, or antisense agents for splice-switching or silencing. Non-limiting examples of RNA-binding proteins are hnRNPA1, hnRNPA2B1, DDX4, ADAD1, DAZL, ELAVL4, IGF2BP3, SAMD4A, TDP43, FUS, FMR1, FXR1, FXR2, EIF4A1-3, the MS2 coat protein, as well as any domains, parts or derivates, thereof. More broadly, particular subclasses of RNA-binding proteins and domains, e.g. mRNA binding proteins (mRBPs), pre-rRNA-binding proteins, tRNA-binding proteins, small nuclear or nucleolar RNA-binding proteins, non-coding RNA-binding proteins, and transcription factors (TFs). Furthermore, various domains and derivatives may also be used as the PoI for transport of an RNA cargo. Non-limiting examples of RNA-binding PoI include small RNA-binding domains (RBDs) (which can be both single-stranded and double-stranded RBDs (ssRBDs and dsRBDs) such as DEAD, KH, GTP_EFTU, dsrm, G-patch, IBN_N, SAP, TUDOR, RnaseA, MMR-HSR1, KOW, RnaseT, MIF4G, zf-RanBP, NTF2, PAZ, RBM1CTR, PAM2, Xpo1, Piwi, CSD, and Ribosomal_L7Ae. Such RNA-binding domains may be present in a plurality, alone or in combination with others, and may also form part of a larger RNA-binding protein construct as such, as long as their key function (i.e. the ability to transport an RNA cargo of interest, e.g. an mRNA or a short RNA) is maintained.

Further as mentioned above, the exosomal polypeptides as per the present invention may be essentially any suitable polypeptide that enables transport of the at least one PoI into an EV. As above-mentioned, the actual localization of the PoI after it has been transported into the EV may vary depending on the nature of the exosomal polypeptide and/or the nature of the PoI, i.e. the PoI may be transported into the lumen of the EV, into the EV membrane, to a membrane-associated location, and/or to any other suitable part of the EV. Non-limiting examples of such exosomal polypeptides are for instance CD81, Itab1, Mfge8, CD63, CD151, Hspg2, Lgals3 bp, Col6a1, Agrn, Tspan14, Lamc1, Lamb1, Tfrc, CD47, CD82, Slit2, Syntenin, Alix, Syndecan, synaptotagmin, Lamp2, Lamp2b, CD13, CD86, Flotillin, Syntaxin-3, LiCAM, LFA-1, Mac-1 alpha and beta, Vti-1A and B, ICAM-1, CD2, CD18, CD37, CD36, CD53, CD82, CXCR4, FcR, CD40, CD40L, CD41a, CD44, CD45, and tetraspanins, GluR2/3, HLA-DM, immunoglobulins, MHC-I or MHC-II and components thereof, and TCR beta, and numerous other polypeptides capable of transporting a polypeptide construct comprising a PoI to an EV.

In yet another embodiment, the EVs of the present invention further comprise at least one targeting moiety. Typically, the targeting moiety is present on the surface of the EV (i.e. protruding from the EV membrane into the extravesicular environment), typically in the form of fusion proteins between the targeting moiety and an EV protein, in order to facilitate reaching the correct tissue or cell type in vivo and/or in vitro. The EVs may also further comprise penetration enhancers, to increase the penetration into selected tissues or compartments. Such penetration enhancers may be peptides or polypeptides expressed on the surface of the EVs as fusion constructs with a suitable exosomal polypeptide. The penetration enhancers may for instance be cell-penetrating peptides (CPPs) (such as Tat, transportan, transportan 10, poly-Arg, MPG, Pep-1, penetratin, etc.), antibodies (which may target cell surface receptors that facilitate internalization, e.g. the transferrin receptor or the insulin receptor), or affibodies, or any other type molecule that would increase the internalization and/or tissue penetration of the EVs. In analogy with the targeting moieties, the penetration enhancers may be expressed on the surface of the EVs through creation of fusion constructs between an exosomal polypeptide and at least one penetration enhancer.

In yet another aspect, the present invention pertains to a highly effective method for producing EVs with strong therapeutic efficacy in large quantities. The methods as per the present invention comprise the steps of (a) introducing into a source cell at least one polynucleotide construct which encodes at least one PoI, an endogenously activatable polypeptide-based release system, and an exosomal polypeptide, and (b) expressing the corresponding polypeptide(s) from the polynucleotide construct(s). Typically, the method also comprises a step (c) of collecting the EVs generated (i.e. released) by the source cell, into which EVs the PoI has been released through endogenous triggering of the protein-based release domain.

The introduction of suitable polynucleotide constructs into a source cell (typically a cell culture comprising a suitable EV-producing cell type for production of EVs) may be achieved using a variety of conventional techniques, such as transfection, virus-mediated transformation, electroporation, etc. Transfection may be carried out using conventional transfection reagents such as liposomes, CPPs, cationic lipids or polymers, calcium phosphates, dendrimers, etc. Virus-mediated transfection is also a highly suitable methodology, and may be carried out using conventional virus vectors such as adenoviral or lentiviral vectors. Virus mediated transformation is particularly relevant when creating stable cell lines for cell banking, i.e. the creation of master cell banks (MCBs) and working cell banks (WCBs) of EV-producing cell sources.

In certain instances, it may be advantageous to introduce more than one polynucleotide construct into the source cells. This may for instance be the case when employing the NLS-NLSBP release system. In such cases, the polypeptide constructs encoded for by the polynucleotide constructs will be translated separately followed by the desired specific interaction between the polypeptides (e.g. a PoI comprising an NLS and an exosomal protein fused to an NLSBP) inside the source cell post translation. If one is on the other hand employing a monomeric system such as a Dendra-based release system or a cis-cleaving release system (e.g. an intein release system) it may be more advantageous to introduce a single polynucleotide construct into the source cell in order to encode for a single polypeptide construct. In a further embodiment, the production of EVs by the cells of the cell culture may be enhanced by exposing the cells to different conditions that may induce increased EV production. Serum starvation, hypoxia, exposure to cytokines such as TNFalpha or interferons, antibiotics such as bafilomycin, and other substances are methods that may be used to increase the EV production, the yield, and also the quality of the EVs.

In further aspects, the present invention also pertains to inventive polynucleotide and polypeptide constructs. The polynucleotide constructs as per the present invention typically comprise nucleotide stretches encoding for at least one PoI, at least one endogenously activatable polypeptide-based release system or a portion of a polypeptide-based release system, and at least one exosomal polypeptide. A non-limiting example would be a polynucleotide construct encoding for an enzyme PoI (such as NPC1 or GBA) for the treatment of a lysosomal storage disorders, a cis-cleaving intein, and an exosomal polypeptide such as CD81, syntenin or CD63. Thus, the present invention naturally also relates to the corresponding polypeptide constructs, i.e. polypeptide constructs comprising at least one PoI, at least one endogenously triggered polypeptide-based release system or a portion of a polypeptide-based release system, and at least one exosomal polypeptide. Furthermore, the present invention also pertains to EV-producing cells (typically cells present in the form of cell culture but also individual cells as such) comprising the above-mentioned polynucleotide construct(s) and/or the above-mentioned polypeptide(s).

In another aspect, the present invention relates to methods for delivery of a PoI into the intracellular environment or into the membrane of a target cell, either in vitro or in vivo. The methods comprise contacting a target cell with an EV comprising either (i) a PoI which is releasably attached to an exosomal polypeptide using an endogenously activatable peptide-based release system or (ii) a PoI which has been released from an exosomal polypeptide, either inside the EV or inside the target cell. Importantly, unlike in the prior art, the PoIs of the present invention are delivered into target cells in a substantially unconjugated form, i.e. a PoI in question is not conjugated to a large exosomal protein (or in the case of a dimeric optogenetic proteins, an optogenetic dimer) that could potentially hamper the activity of the PoI. For instance, WO2014/168548 teaches exosomes comprising therapeutic polypeptides of interest that are conjugated to exosomal proteins, which is an excellent strategy for certain types of therapeutic proteins that are capable of exerting their intended activity despite being conjugated to an exosomal protein. However, the methods of the present invention enable delivery of a much wider range of therapeutic PoIs, through the inventive controllable endogenously activatable release systems which liberate the PoIs in their desired location(s) without the need for any exogenous stimuli.

In certain embodiments as per the present invention, the PoI may be an integral membrane protein conjugated to an exosomal polypeptide with the aid of the endogenously triggered protein-based release systems. An integral membrane PoI may be presented on the outer, inner or both surfaces of an EV. Without wishing to be bound by any theory, it is surmised that following uptake into a target cell, an EV—comprising a polypeptide construct which in turn comprises an integral membrane PoI—is trafficked to the endoplasmic reticulum (ER). The contents of the EV, i.e. the polypeptide construct comprising the integral membrane PoI, may be processed and sorted at the ER followed by ER-mediated trafficking to the appropriate compartment of the target cell. Thus, a polypeptide construct comprising an exosomal protein conjugated with the aid of a polypeptide-based release system to an integral plasma membrane protein (for instance a G-protein coupled receptor (GPCR)) would be routed to the plasma membrane of a target cell, whereas a membrane protein natively present in a lysosomal membrane (i.e. a lysosomal membrane protein) would be routed to a lysosome of the target cell. One particularly important example of a membrane PoI is NPC1, which is a membrane transporter of cholesterol and which when defect results in the storage disorder Niemann-Pick's disease.

The release of the PoI is as above-outlined mediated by an endogenously activatable polypeptide-based release system which is fused to the PoI and/or to the exosomal polypeptide. In an advantageous embodiment, the polynucleotide construct encoding for the subsequent polypeptide construct is designed in such a way so as to place the release system in between the PoI and the exosomal polypeptide. This arrangement enables easy manufacturing of the constructs and efficient release of the PoI in the desired location.

In yet another aspect, the present invention pertains to pharmaceutical compositions comprising EVs in accordance with the present invention. Typically, the pharmaceutical compositions as per the present invention comprise at least one type of therapeutic EV (i.e. a population of EVs having comprising a certain desired PoI) formulated with at least one pharmaceutically acceptable excipient. The at least one pharmaceutically acceptable excipient may be selected from the group comprising any pharmaceutically acceptable material, composition or vehicle, for instance a solid or liquid filler, a diluent, an excipient, a carrier, a solvent or an encapsulating material, which may be involved in e.g. suspending, maintaining the activity of or carrying or transporting the therapeutic delivery vesicles from one organ, or portion of the body, to another organ, or portion of the body (e.g. from the blood to any tissue and/or organ and/or body part of interest).

The present invention also relates to cosmetic applications of the EVs comprising PoIs. Thus, the present invention pertains to skin care products such as creams, lotions, gels, emulsions, ointments, pastes, powders, liniments, sunscreens, shampoos, etc., comprising a suitable EV, in order to improve and/or alleviate symptoms and problems such as dry skin, wrinkles, folds, ridges, and/or skin creases. In one embodiment of both cosmetic and therapeutic nature, the EVs as per the present invention may comprise a botulinum toxin (e.g. botox, for instance botulinum toxin types A-G) as the PoI (botulinum toxins may not necessarily be used only for cosmetic applications but could also be applied for e.g. treatment of migraine headaches and dystonia). In a preferred embodiment, EVs (which comprise a at least one type of PoI) obtainable from a suitable exosome-producing cell with regenerative properties (such as a mesenchymal stem cell) are comprised in a cosmetic cream, lotion, or gel for use in the cosmetic or therapeutic alleviation of wrinkles, lines, folds, ridges and/or skin creases.

In yet another aspect, the present invention relates to EVs as per the present invention for use in medicine. Naturally, when an EV comprising a PoI in accordance with the present invention is used in medicine, it is in fact normally a population of EVs that is being used. The dose of EVs administered to a patient will depend on the amount of PoI that has been loaded into the EV, the disease or the symptoms to be treated or alleviated, the administration route, the pharmacological action of the PoI itself, as well as various other parameters of relevance.

The EVs of the present invention may be used for prophylactic and/or therapeutic purposes, e.g. for use in the prophylaxis and/or treatment and/or alleviation of various diseases and disorders. A non-limiting sample of diseases wherein the EVs as per the present invention may be applied comprises Crohn's disease, ulcerative colitis, ankylosing spondylitis, rheumatoid arthritis, multiple sclerosis, systemic lupus erythematosus, sarcoidosis, idiopathic pulmonary fibrosis, psoriasis, tumor necrosis factor (TNF) receptor-associated periodic syndrome (TRAPS), deficiency of the interleukin-1 receptor antagonist (DIRA), endometriosis, autoimmune hepatitis, scleroderma, myositis, stroke, acute spinal cord injury, vasculitis, Guillain-Barré syndrome, acute myocardial infarction, ARDS, sepsis, meningitis, encephalitis, liver failure, kidney failure, graft-vs-host disease, Duchenne's muscular dystrophy and other muscular dystrophies, lysosomal storage diseases such as Gaucher disease, Fabry's disease, MPS I, II (Hunter syndrome), and III, Niemann-Pick disease, Pompe disease, etc., neurodegenerative diseases including Alzheimer's disease, Parkinson's disease, Huntington's disease and other trinucleotide repeat-related diseases, dementia, ALS, cancer-induced cachexia, anorexia, diabetes mellitus type 2, and various cancers.

Virtually all types of cancer are relevant targets for the present invention, for instance, Acute lymphoblastic leukemia (ALL), Acute myeloid leukemia, Adrenocortical carcinoma, AIDS-related cancers, AIDS-related lymphoma, Anal cancer, Appendix cancer, Astrocytoma, cerebellar or cerebral, Basal-cell carcinoma, Bile duct cancer, Bladder cancer, Bone tumor, Brainstem glioma, Brain cancer, Brain tumor (cerebellar astrocytoma, cerebral astrocytoma/malignant glioma, ependymoma, medulloblastoma, supratentorial primitive neuroectodermal tumors, visual pathway and hypothalamic glioma), Breast cancer, Bronchial adenomas/carcinoids, Burkitt's lymphoma, Carcinoid tumor (childhood, gastrointestinal), Carcinoma of unknown primary, Central nervous system lymphoma, Cerebellar astrocytoma/Malignant glioma, Cervical cancer, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Extracranial germ cell tumor, Extragonadal Germ cell tumor, Extrahepatic bile duct cancer, Eye Cancer (Intraocular melanoma, Retinoblastoma), Gallbladder cancer, Gastric (Stomach) cancer, Gastrointestinal Carcinoid Tumor, Gastrointestinal stromal tumor (GIST), Germ cell tumor (extracranial, extragonadal, or ovarian), Gestational trophoblastic tumor, Glioma (glioma of the brain stem, Cerebral Astrocytoma, Visual Pathway and Hypothalamic glioma), Gastric carcinoid, Hairy cell leukemia, Head and neck cancer, Heart cancer, Hepatocellular (liver) cancer, Hodgkin lymphoma, Hypopharyngeal cancer, Intraocular Melanoma, Islet Cell Carcinoma (Endocrine Pancreas), Kaposi sarcoma, Kidney cancer (renal cell cancer), Laryngeal Cancer, Leukemias ((acute lymphoblastic (also called acute lymphocytic leukemia), acute myeloid (also called acute myelogenous leukemia), chronic lymphocytic (also called chronic lymphocytic leukemia), chronic myelogenous (also called chronic myeloid leukemia), hairy cell leukemia)), Lip and Oral, Cavity Cancer, Liposarcoma, Liver Cancer (Primary), Lung Cancer (Non-Small Cell, Small Cell), Lymphomas ((AIDS-related lymphoma, Burkitt lymphoma, cutaneous T-Cell lymphoma, Hodgkin lymphoma, Non-Hodgkin (an old classification of all lymphomas except Hodgkin's) lymphoma, Primary Central Nervous System lymphoma)), Medulloblastoma, Merkel Cell Carcinoma, Mesothelioma, Metastatic Squamous Neck Cancer with Occult Primary, Mouth Cancer, Multiple Endocrine Neoplasia Syndrome, Multiple Myeloma/Plasma Cell Neoplasm, Mycosis Fungoides, Myelodysplastic/Myeloproliferative Diseases, Myelogenous Leukemia, Chronic Myeloid Leukemia (Acute, Chronic), Myeloma, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, Pancreatic islet cell cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Pleuropulmonary blastoma, Prostate cancer, Rectal cancer, Renal cell carcinoma (kidney cancer), Retinoblastoma, Rhabdomyosarcoma, Salivary gland cancer, Sarcoma (Ewing family of tumors sarcoma, Kaposi sarcoma, soft tissue sarcoma, uterine sarcoma), Sezary syndrome, Skin cancer (nonmelanoma, melanoma), Small intestine cancer, Squamous cell, Squamous neck cancer, Stomach cancer, Supratentorial primitive neuroectodermal tumor, Testicular cancer, Throat cancer, Thymoma and Thymic carcinoma, Thyroid cancer, Transitional cell cancer of the renal pelvis and ureter, Urethral cancer, Uterine cancer, Uterine sarcoma, Vaginal cancer, Vulvar cancer, WaldenstrOm macroglobulinemia, and/or Wilm's tumor.

The EVs as per the present invention may be administered to a human or animal subject via various different administration routes, for instance auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intraabdominal, intra-amniotic, intra-arterial, intra-articular, intrabiliary, intrabronchial, intrabursal, intracardiac, intracartilaginous, intracaudal, intracavernous, intracavitary, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intrailleal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes.

In a further aspect, the present invention relates to, as above-mentioned, a method of producing EVs (or more accurately producing populations of EVs) comprising the steps of (a) introducing into a cell source (typically a cell culture) one or more polynucleotide construct(s) encoding at least one PoI, an endogenously activatable polypeptide-based release system, and an exosomal polypeptide, (b) expressing the polypeptide construct(s) encoded by the polynucleotide construct(s), and (c) collecting EVs generated by the cell. If one utilizes the monomeric light-induced cleave system for releasing the PoI then an additional step of short-term exposing the EVs to light of a suitable wavelength is added to the production method. The light exposure step can take place while the EVs are still being formed inside cells, when the EVs have just been released into the cell culture medium, when EVs have been processed further (for instance by tangential flow filtration (TFF), ultrafiltration, bead-elute chromatography, size-exclusion chromatography or any combination thereof), or essentially whenever suitable depending on the cell source, the characteristics of the EV production, and the EVs per se. Suitable culture systems include conventional 2D cell culture, 3D cell culture, bioreactors, hollow-fiber bioreactors, etc.

The method may also comprise exposing the source cells to serum starvation, hypoxia, bafilomycin, or cytokines such as TNF-alpha and/or IFN-gamma, in order to influence the yield or properties of the resulting EVs. The EV production scale and timeline will be heavily dependent on the EV-producing cell or cell line and may thus be adapted accordingly by a person skilled in the art.

The production methods may further comprise a purification step, wherein the EVs are purified through a procedure selected from the group comprising liquid chromatography (LC), bead-elute LC, size-exclusion LC, high-performance liquid chromatography (HPLC), spin filtration, tangential flow filtration, hollow fiber filtration, centrifugation, immunoprecipitation, etc, or any combination thereof.

In an advantageous embodiment, the purification of the EVs is carried out using a sequential combination of filtration (preferably ultrafiltration (UF), tangential flow filtration (TFF) or hollow fiber filtration) and bead-elute or size exclusion liquid chromatography (LC). This combination of purification steps results in optimized purification, which in turn leads to superior therapeutic activity. Further, as compared to ultracentrifugation (UC), which is routinely employed for purifying exosomes, sequential filtration-chromatography is considerably faster and possible to scale to higher manufacturing volumes, which is a significant drawback of the current UC methodology that dominates the prior art.

It shall be understood that the above described exemplifying aspects, embodiments, alternatives, and variants can be modified without departing from the scope of the invention. The invention will now be further exemplified with the enclosed examples, which naturally also can be modified considerably without departing from the scope and the gist of the invention.

Experimental Part

Materials and Methods
Construct Design and Cloning
Various cis-cleaving endogenously activatable polypeptide-based release systems (such as slow-cleaving inteins, fast-cleaving inteins, sortase A and FrpC) have been assessed, in combination with several PoIs (such as Cre, NPC1, IL10, RNA-binding MS2 coat protein) and exosomal polypeptides (CD81, CD63, CD9, syntenin, syndecan, Alix, CD133, etc.). Similarly, various NLS-NLSBP release systems and monomeric light induced-release systems were assessed, together with PoIs and EV proteins. NLS-NLSBP systems include: KPNA1-NRF2, KPNA6-STAT3, KPNB1-STAT3, KPNA2-HSF1. NLSBPs include importins from the importin alpha and beta families, and other NLS binding proteins, including KPNA1, KPNA2, IPO8, TPNO1, HIKE-SHI, SNUPN, HEATR3, and other RAN binding proteins. NLS containing proteins include various transcription factors, nucleases and other nuclear proteins such as bHLH, MyoD, cMyc, HSF1, STAT3, p53, NFkB, Cas9, HSP70, and U1 snRNP. Monomeric light-induced cleavage systems include: Kaede, KikGR, EosFP, and Dendra. PoIs include NPC1, GBA, AGAL, Huntingtin, BDNF, an NFkB super-repressor, RNA-binding proteins and domains such as hnRNPA1, the MS2 coat protein, G-patch, etc. In the case of RNA-binding proteins, these have been combined with a polynucleotide of interest, which said RNA-binding proteins drag into the EV. A large number of exosomal proteins have been evaluated: CD81, CD63, CD9, syndecan, Alix, CD133, Syntenin-1, Syntenin-2, Lamp2b, TSPAN8, and TSPAN14, as well as variants and domains thereof.

When evaluating the cis-cleaving release system constructs and the monomeric light-induced cleavage systems, ORFs were typically generated by synthesis and cloned into the mammalian expression vector pSF-CAG-Amp. Briefly, synthesized DNA and vector plasmid were digested with enzymes NotI and SalI as per manufacturers instruction (NEB). Restricted, purified DNA fragments were ligated together using T4 ligase as per manufacturers instruction (NEB). Successful ligation events were selected for by bacterial transformation on ampicillin-supplemented plates. Plasmid for transfection was generated by 'maxi-prep', as per manufacturers instruction.

In the case of the NLS-NLSBP release system, ORF sequences were normally purchased (Origene Technologies, Inc.) and amplified and cloned into the MSC A site of pIRES bicistronic expression vector (Clonetech, Laboratories Inc.) such that upon translation the NLSBP protein was expressed as a chimera, fused to the exosomal polypeptide. NLS were either fused onto PoIs lacking NLS, or when already present on the PoI used as-is, occasionally with genetic modifications. Most of the cloning was performed using the NEBuilder HiFi DNA Assembly Cloning Kit (NEB, Inc.) and confirmed using Sanger sequencing (Source BioScience). The pIRES vector enables bicistronic expression of both transgenes simultaneously, ensuring EV-producing cells would express both transgenes simultaneously. Plasmids were transformed into the NEB 5-alpha Competent *E. coli* cells (NEB, Inc.) and grown overnight in a shaking incubator according to manufacturer's recommendations. Plasmids were isolated and purified using the 'maxi-prep' kit, as per manufacturer's instruction (Macherey-Nagel).

Cell Culture and Transfection

Depending on the experimental design and assays, in certain cases, non-viral transient transfection and exosome production was carried out in conventional 2D cell culture, whereas in other cases virus-mediated transduction was employed to create stable cell lines, which were typically cultured in bioreactors of different type. For conciseness, only a few examples are mentioned herein.

HEK293T cells were typically seeded into 15 cm dishes ($9 \times 10^6$ cells per dish) and left overnight in serum-containing DMEM as recommended by ATCC. The following day the cells were transiently transfected with lipoplexed DNA added directly onto cells. Briefly, DNA and polyethylene-imine (PEI) were separately incubated in OptiMEM for 5 minutes before combining together for 20 minutes at room temperature. Lipoplexed DNA and cells were co-incubated for 6 hours following which conditioned culture media was changed to OptiMEM for 48 hours. Other cells and cell lines that were evaluated in dishes, flasks and other cell culture vessels included bone marrow-derived mesenchymal stromal cells (BM-MSCs) and Wharton's jelly-derived MSCs (WJ-MSCs), amnion cells, fibroblasts, various endothelial and epithelial cells, as well as various immune cells and cell lines.

In the case of viral transduction and creation of stable cell lines for various combinations of PoI, release system, and exosomal polypeptide, cell sources such as BM-MSCs, WJ-MSC, fibroblasts, amnion cells, fibroblasts, various endothelial and epithelial cells, were virus-transduced, typically using lentivirus (LV). Typically, 24 hours before infection, 100.000 cells (e.g. fibroblasts, MSCs, etc.) or 200.000 cells (e.g. HEK293T) are plated in a 6-well plate. 2 uL of LV and optionally Polybrene (or hexadimethrine bromide, final concentration on the well of 8 ug/mL) are added, and 24 hours post transduction the cell medium of transduced cells is changed to fresh complete media. At 72 hours post transduction, puromycin selection (4-6 µg/ml) is performed, normally for 7 days followed by analysis of stable expression of the polypeptide construct.

Stable cells were cultured in either 2D culture or in bioreactors, typically hollow-fiber bioreactors, and conditioned media was subsequently harvested for exosome preparation. Various preparation and purification steps were carried out. The standard workflow comprises the steps of pre-clearing of the supernatant, filtration-based concentration, chromatography-based removal of protein contaminants, and optional formulation of the resultant exosome composition in a suitable buffer for in vitro and/or in vivo assays.

Assays and Analytics

Figure 14:
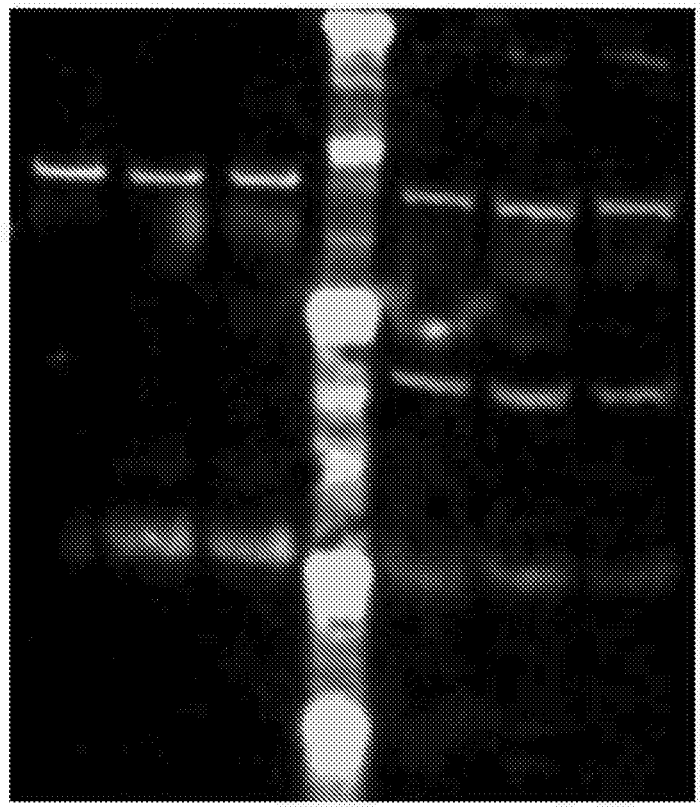
FIG. 14 shows an illustration of a Western blot analysis of Cre recombinase enrichment within exosomes using an intein-based polypeptide releasable system. Lanes 1-3 shows exosomes and lanes 5-7 their respective whole cell lysate. Lane 1 and 5—Soluble NLSCre; Lanes 2&6 CD63-intein-Cre; Lanes 3&7 CD63-intein-NLSCre; 4 protein ladder. Alix loading control; Cre recombinase.

Western blot is a highly convenient analytical method to evaluate the enrichment of PoIs in EVs. Briefly, SDS-PAGE was performed according to manufacturer's instruction (Invitrogen, Novex PAGE 4-12% gels), whereby $1 \times 10^{10}$ exosomes and 20 ug cell lysate were loaded per well. Proteins from the SDS-PAGE gel were transferred to PVDF membrane according to manufacturer's instruction (Immobilon, Invitrogen). Membranes were blocked in Odyssey blocking buffer (Licor) and probed with antibodies against PoI and the exosomal protein according to supplier's instruction (Primary antibodies—Abcam, Secondary antibodies—Licor). Molecular probes visualized at 680 and 800 nm wavelengths. FIG. 14 shows an illustration of this for the combination of Cre recombinase as the PoI and Alix as the exosomal protein.

For EV size determination, nanoparticle tracking analysis (NTA) was performed with a NanoSight instrument equipped with analytical software. For all recordings, we used a camera level of 13 or 15 and automatic function for all post-acquisition settings. Electron microscopy and fluorescence microscopy were frequently used to understand PoI location and release and to quantitate and analyze EVs.

EVs were isolated and purified using a variety of methods, typically a combination of filtration such as TFF and LC. Typically, EV-containing media was collected and subjected to a low speed spin at 300 g for 5 minutes, followed by 2000 g spin for 10 minutes to remove larger particles and cell debris. The supernatant was then filtered with a 0.22 µm syringe filter and subjected to different purification steps. Large volumes were diafiltrated and concentrated to roughly 20 ml using the Vivaflow 50R tangential flow (TFF) device (Sartorius) with 100 kDa cutoff filters or the KR2i TFF system (SpectrumLabs) with 100 or 300 kDa cutoff hollow fibre filters. The preconcentrated medium was subsequently loaded onto the bead-eluate columns (HiScreen or HiTrap Capto Core 700 column, GE Healthcare Life Sciences), connected to an ÄKTAprime plus or ÄKTA Pure 25 chromatography system (GE Healthcare Life Sciences). Flow rate settings for column equilibration, sample loading and column cleaning in place procedure were chosen according to the manufacturer's instructions. The sample was collected according to the UV absorbance chromatogram and concentrated using an Amicon Ultra-15 10 kDa molecular weight cut-off spin-filter (Millipore) to a final volume of 100 µl and stored at −80° C. for further downstream analysis. To assess the protein and RNA elution profiles, media was concentrated and diafiltrated with KR2i TFF system using 100 kDa and 300 kDa hollow fibre filters and a sample analysed on a Tricorn 10/300 Sepharose 4 Fast Flow (S4FF) column (GE Healthcare Life Sciences).

Examples

Figure 3:
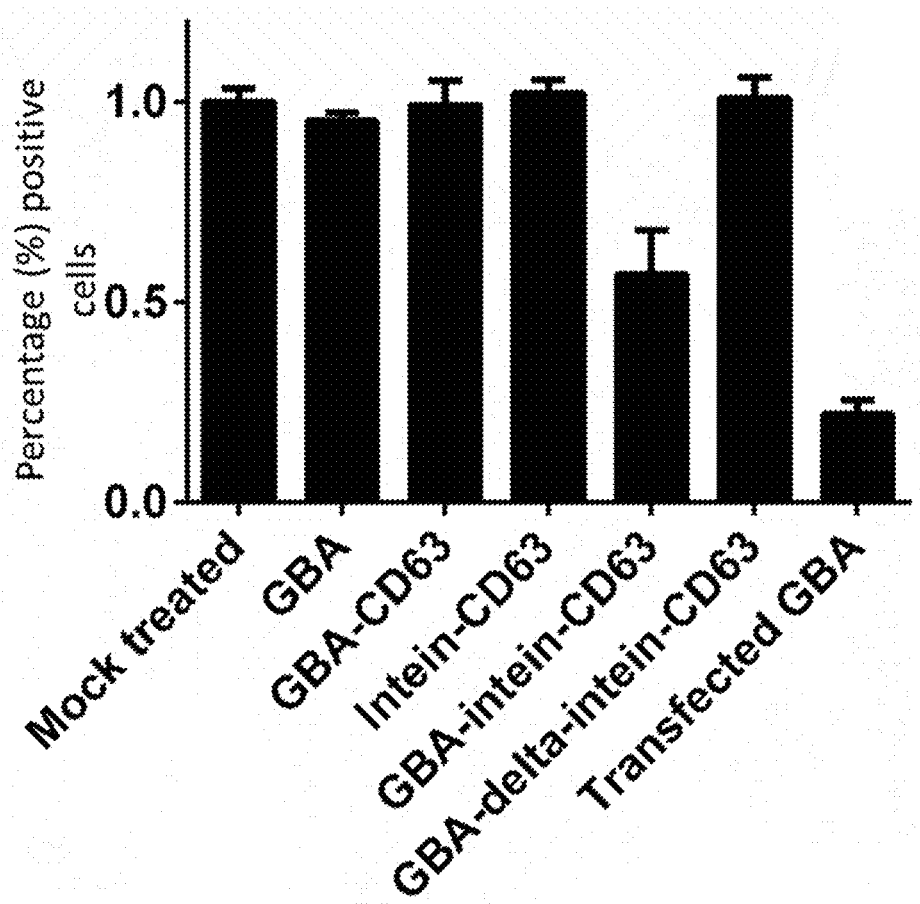
FIG. 3 shows the results of GBA-deficient cells treated with EVs enriched with intein-GBA enriched fusion proteins. Recipient cells experience a decrease in glucocerebroside levels following the delivery of bioactive GBA. A similar experiment was carried out with the transporter NPC1 in NPC1-deficient fibroblasts.
Figure 4:
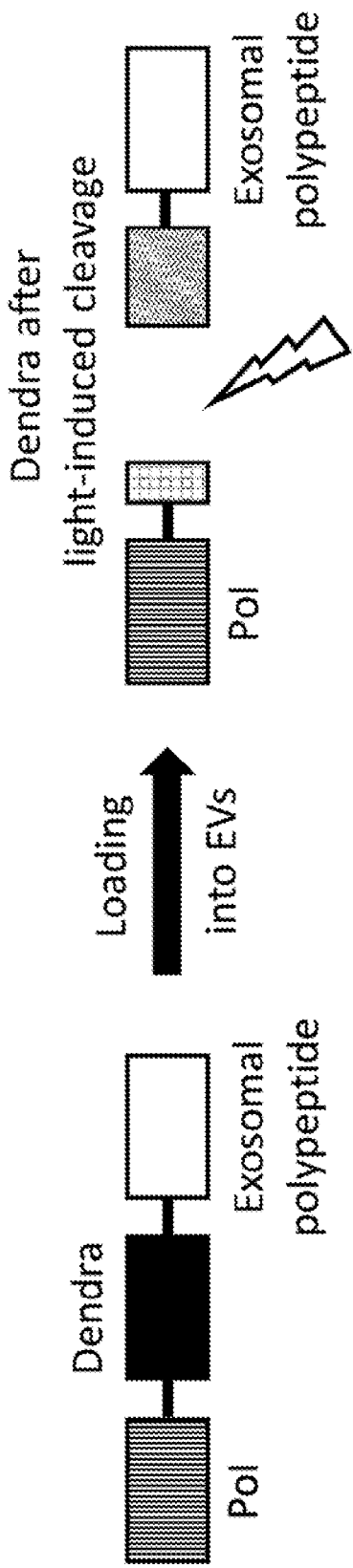
FIG. 4 depicts a polypeptide construct comprising a light-induced cleavage release system based on the GFP-like Dendra protein for releasing a PoI. Dendra is a monomeric release system that can be activated by a short-term boost of light.

FIG. 3 shows the results of GBA-deficient patient-derived lymphocytes treated with BM-MSC EVs enriched with a polypeptide construct comprising a slow-cleaving intein inserted between the GBA enzyme and the exosomal protein CD63. Using an HPLC-based assay, recipient cells were shown to display a decrease in the levels of the lipid glucocerebroside following the EV-mediated delivery of freely released GBA. A similar experiment was carried out using a polypeptide construct comprising as PoI the lipid transporter protein NPC1, a fast-cleaving intein-based release system, and the exosomal protein CD133. EVs comprising this polypeptide construct efficiently delivered NPC1 to NPC1-deficient fibroblasts, leading to a significantly higher level of functional cholesterol transport as opposed to control EVs comprising a non-functional release system.

In another example, an endogenously activatable N-terminus protease-based release system was used to fuse the PoI p53 to the exosomal protein syndecan, with fibroblasts as the EV-producing parental cell. EV-mediated endogenously actived releasable delivery of p53 into MDA-MB-231 cancer cells in vitro was significantly more effective than non-releasable delivery using the same EV polypeptide construct.

Figure 5:
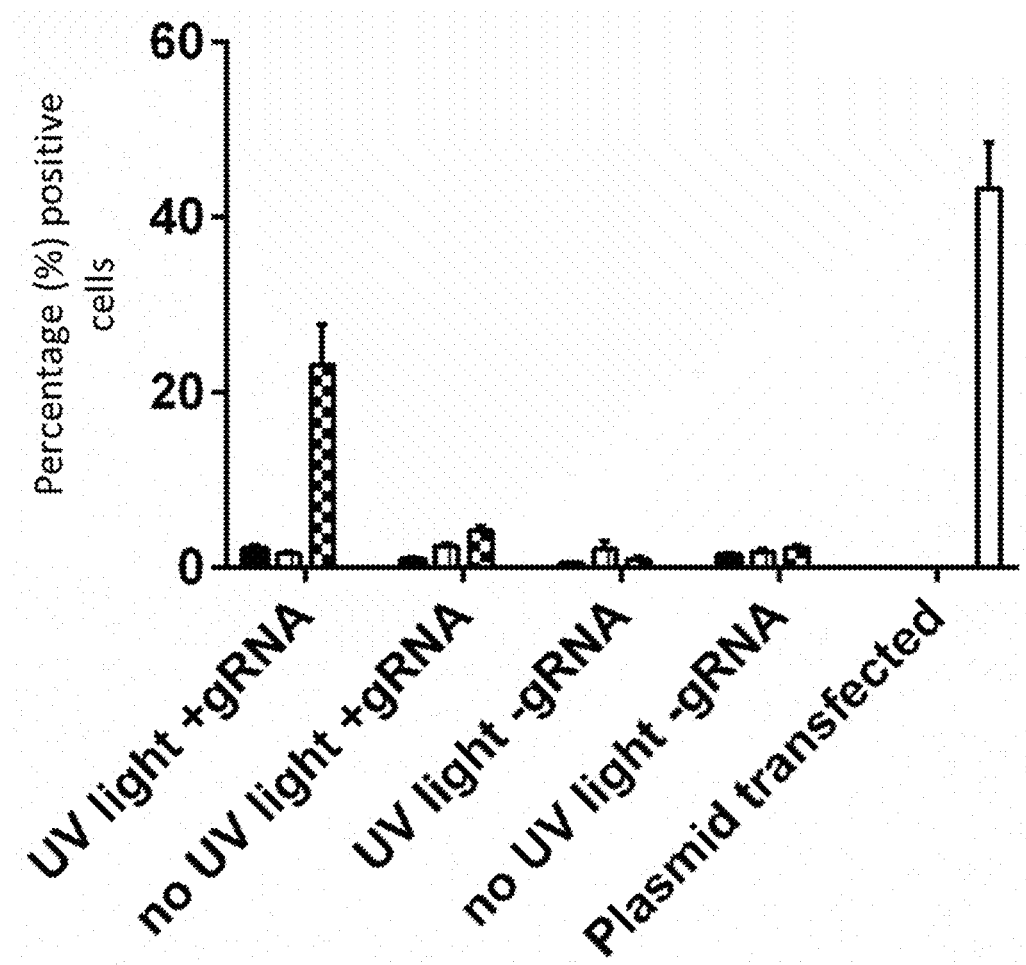
FIG. 5 shows the results of a non-homologous end-joining (NHEJ) assay. HEK293T-red cells containing a reporter system were transfected with exosomes comprising guide RNA (gRNA) and a polypeptide construct comprising CD81 as the exosomal polypeptide, Kaede as the monomeric light-induced cleavage-based release system, and Cas9 as the PoI. Exosomes where obtained from a cell culture that either was or was not exposed to a short-term boost of blue light during the exosome production process. Only exosomes obtained from cells exposed to light—which induced cleavage of the Kaede and thereby release of Cas9—showed an increase in the percentage of positive cells.
Figure 6:
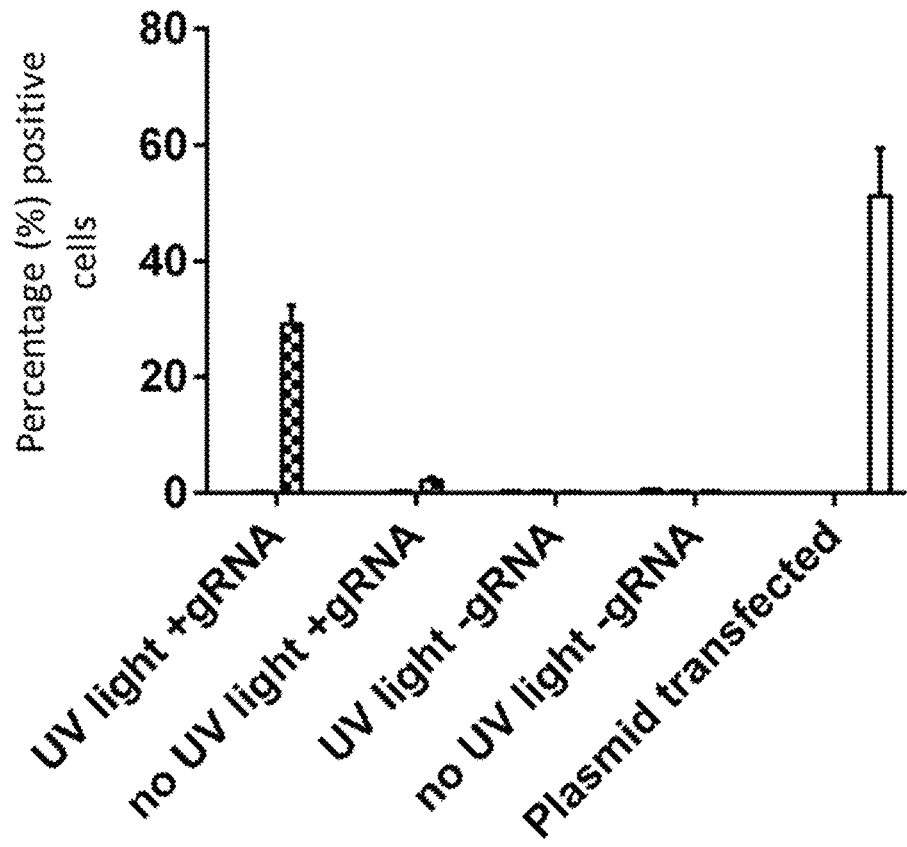
FIG. 6 shows the results of a High Resolution Melting (HRM) analysis of cells treated with EVs harvested from cells exposed to light. EVs comprising the same polypeptide construct as in FIG. 5 induced Cas9-mediated mutations in the AAVS locus as a result of efficient intracellular delivery of bioactive Cas9 and gRNA.
Figure 7:
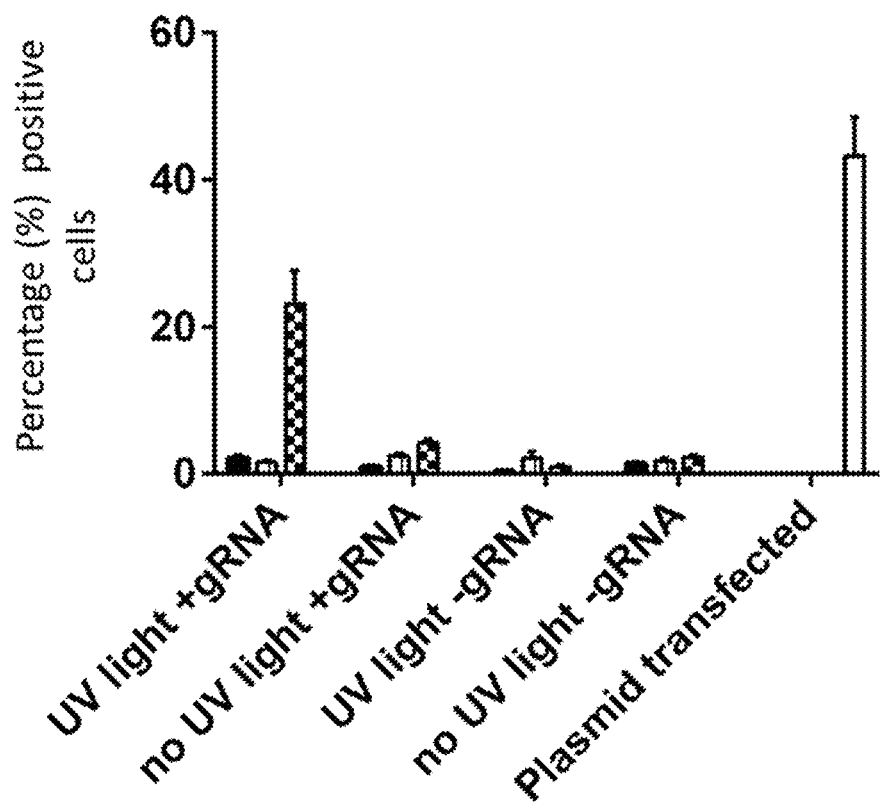
FIG. 7 shows the effects in the NHEJ assay of EVs comprising a polypeptide construct comprising Cas9 fused to CD63 through the monomeric light-induced release polypeptide Dendra2, which renders functional Cas9 in EVs after UV/blue light irradiation.
Figure 8:
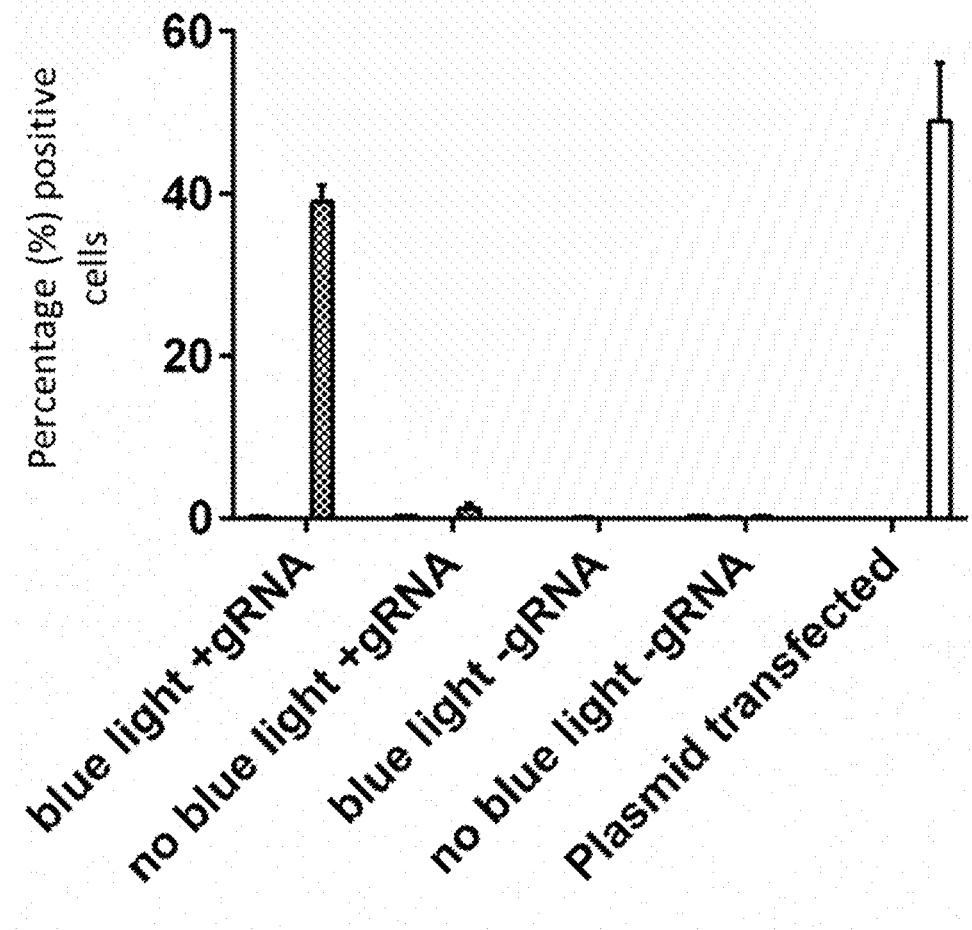
FIG. 8 shows HRM results of cells treated with EVs harvested from cells exposed to UV/blue light. EVs comprising the same polypeptide construct as in FIG. 7 induced Cas9-mediated mutations in the AAVS locus as a result of efficient intracellular delivery of bioactive Cas9 and gRNA.
Figure 9:
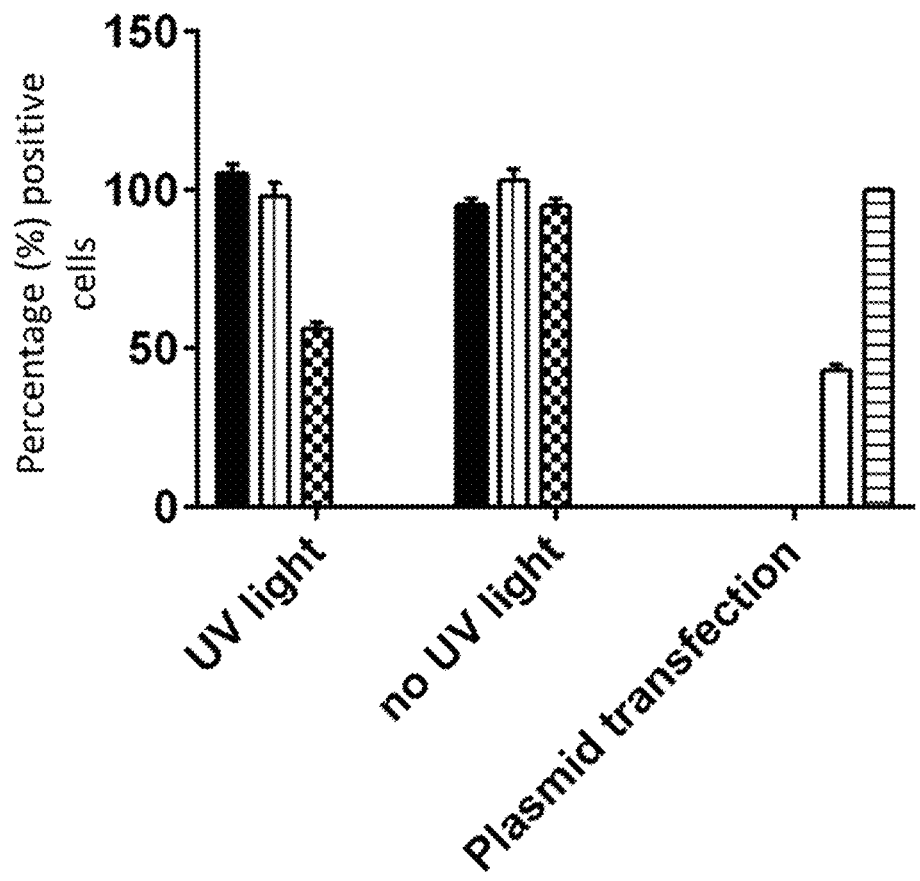
FIG. 9 shows robust down regulation of NfKB response achieved by EVs loaded with a WASP-targeted single-chain variable fragment (scFv)-KikGR-CD63 polypeptide construct, exposed to UV-light to release the scFv inside the target bone marrow-derived macrophage cell.

FIG. 5 shows the results of a non-homologous end-joining (NHEJ) assay. HEK293T-red cells containing a reporter system were transfected with fibroblast-derived EVs comprising guide RNA (gRNA) and a polypeptide construct comprising CD81 as the exosomal polypeptide, Kaede as the monomeric light-induced cleavage-based release system, and Cas9 as the PoI. EVs where obtained from a cell culture that either was or was not exposed to blue light during the exosome production process. Only exosomes obtained from cells exposed to a short boost of light—which induced cleavage of Kaede and thereby release of Cas9—showed an increase in the percentage of positive cells. Similarly, FIG. 6 shows the results of a High Resolution Melting (HRM) analysis of cells treated with EVs harvested from cells exposed to light. Fibroblast EVs comprising the same polypeptide construct as in FIG. 5 induced Cas9-mediated mutations in the AAVS locus as a result of efficient intracellular delivery of bioactive Cas9 and gRNA. FIG. 7 shows the effects in the NHEJ assay of amnion epithelial cell-derived EVs comprising a polypeptide construct comprising Cas9 fused to CD63 through the monomeric light-induced release polypeptide Dendra2, which renders functional Cas9 in EVs after UV/blue light irradiation. FIG. 8 shows HRM results of cells treated with WJ-MSC EVs harvested from cells exposed to UV/blue light. EVs comprising the same polypeptide construct (but this time in WJ-MSC-derived EVs) as in FIG. 7 induced Cas9-mediated mutations in the AAVS locus as a result of efficient intracellular delivery of bioactive Cas9 and gRNA. FIG. 9 shows robust down regulation of NfKB response achieved by HEK EVs loaded with a WASP-targeted single-chain variable fragment (scFv)-KikGR-CD63 polypeptide construct, exposed to UV-light to release the scFv inside the target bone marrow-derived macrophage cell.

Figure 10:
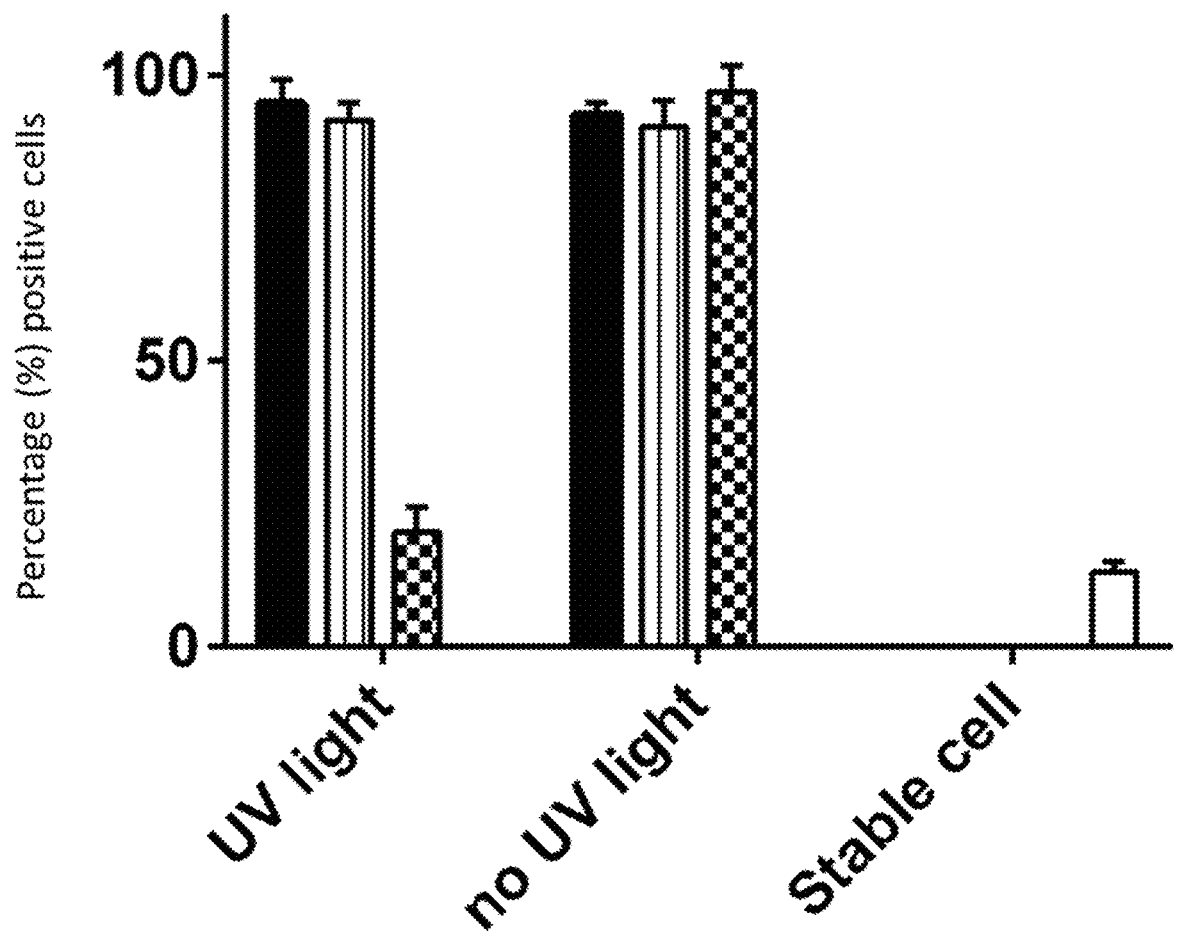
FIG. 10 shows the results of Jurkat cells stimulated to express the IL2-receptor and at the same time treated with EVs loaded with a scFv towards the IL2R-alpha subunit. Only the positive control and the EVs loaded with scFv-Dendra2-CD63 (and exposed to UV-light) induced a down regulation of the IL2R on the cell surface of the Jurkat cells, according to FACS analysis.
Figure 11:
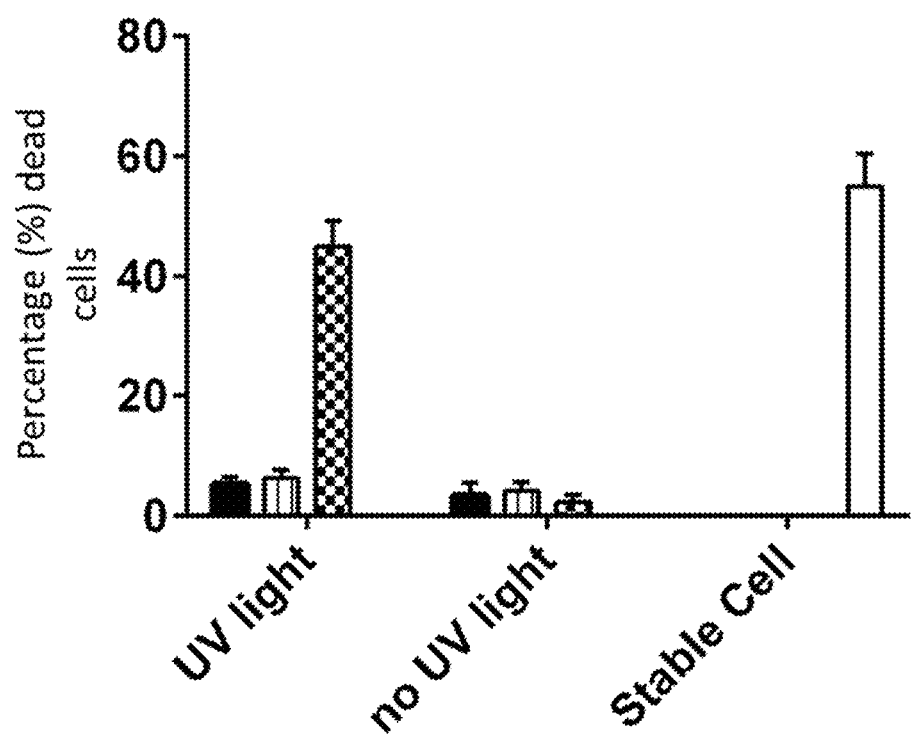
FIG. 11 shows the results of the erbB-2-positive ovarian carcinoma cell line SKOV3 treated with EVs loaded with a scFv targeted towards the oncoprotein erb-2. Cell death was assayed at 48 hours after treatment. Only EVs loaded with scFv-Dendra2-CD63 (and thereafter exposed to UV-light) induced cell death in comparable levels to the positive control.

FIG. 10 shows the results of Jurkat cells stimulated to express the IL2-receptor and at the same time treated with HEK EVs loaded with a scFv towards the IL2R-alpha subunit. Only the positive control and the EVs loaded with scFv-Dendra2-CD63 (and exposed to UV-light) induced a down regulation of the IL2R on the cell surface of the Jurkat cells, according to FACS analysis. FIG. 11 shows the results of the erbB-2-positive ovarian carcinoma cell line SKOV3 treated with EVs loaded with a scFv targeted towards the oncoprotein erb-2. Cell death was assayed at 48 hours after treatment. Only EVs loaded with scFv-Dendra2-CD63 (and thereafter briefly exposed to UV-light) induced cell death in comparable levels to the positive control.

Figure 12:
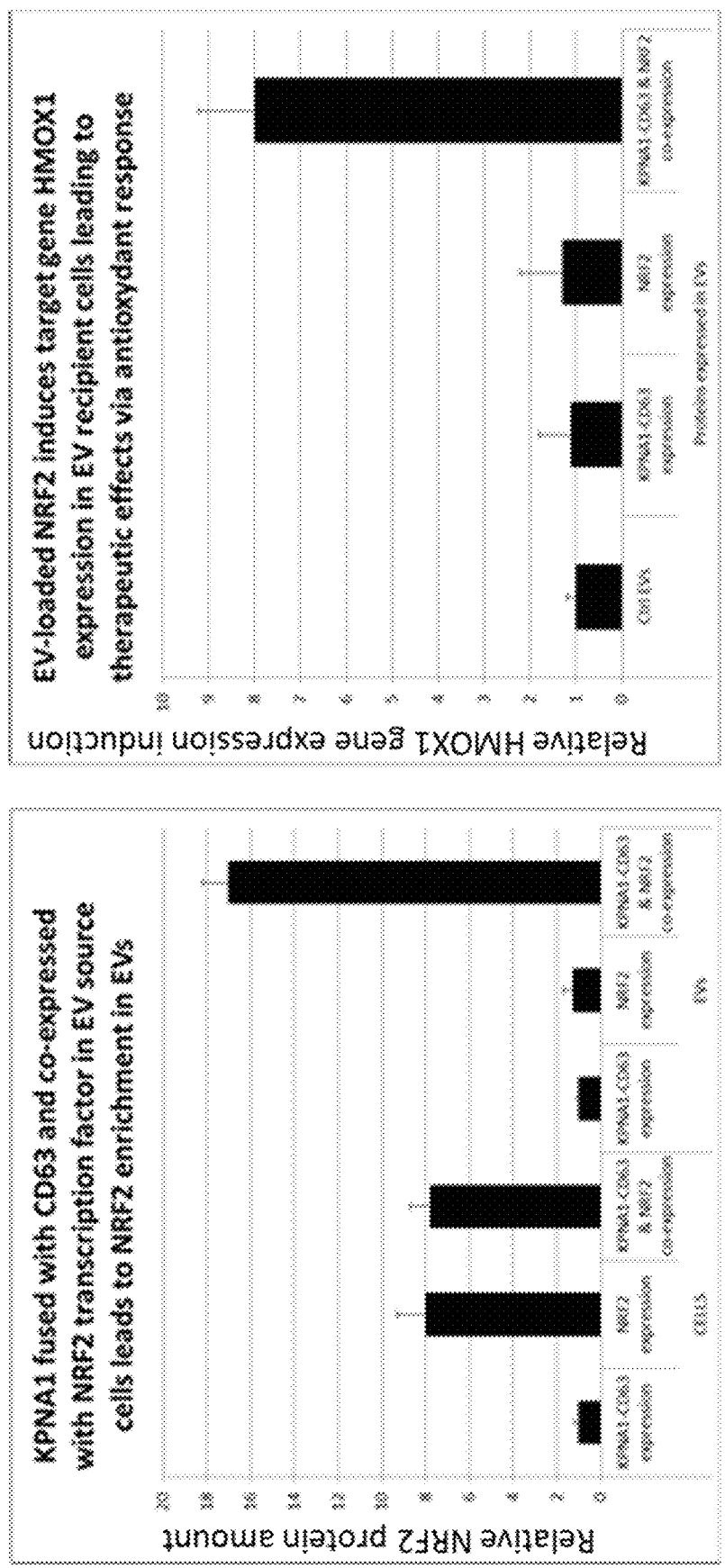
FIG. 12 shows the results of loading NRF2 transcription factor to EVs using the NLSBP-NLS-based release system and the associated effects in inducing target gene HMOX1 expression in recipient cells. An NLSBP (KPNA1 a.k.a. importin α5) was fused to exosomal protein CD63 and co-expressed in EV source cells (various types of immune cells were tested with good results) with NRF2. Co-expression leads to significantly enhanced EV sorting of NRF2, as estimated by Western blotting as compared to expression of NRF2 alone. Delivery of NRF2 loaded EVs using this strategy leads to induction of target gene expression in EV recipient cells.
Figure 13:
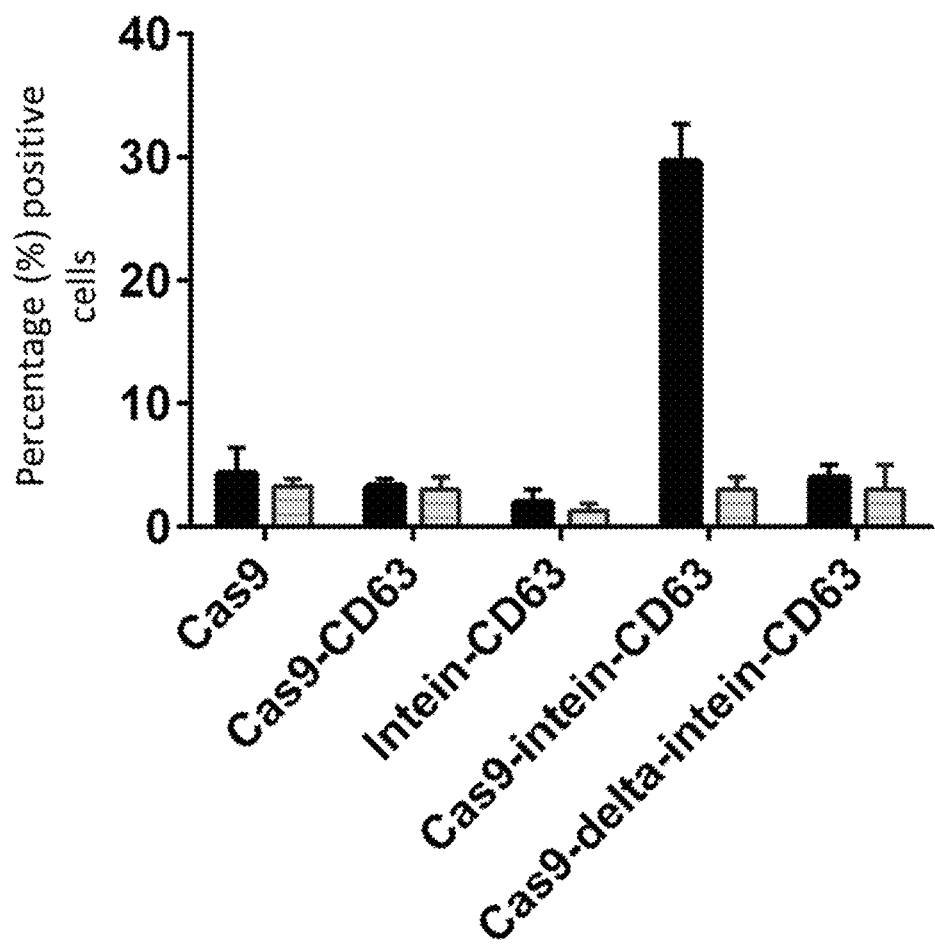
FIG. 13 shows a similar experiment as in FIG. 5, but here with a cis-cleaving intein (comprising the amino acid sequence Val-Val-Val-His-Asn (SEQ ID NO: 1)) as a release system fused to CD63, CD81 (data not shown), and syntenin (data not shown) and to Cas9. As can be seen from FIG. 13, only the unmutated intein induced relevant levels of NHEJ.

FIG. 12 shows the results of loading NRF2 transcription factor to BM-MSC-derived EVs using the NLSBP-NLS-based release system and the associated effects in inducing target gene HMOX1 expression in recipient cells. An NLSBP (KPNA1, also known as importin α5) was fused to the exosomal protein CD63 and co-expressed in EV source cells (in addition to BM-MSCs, various types of immune cells were tested with good results) with NRF2. Co-expression leads to significantly enhanced EV sorting of NRF2, as estimated by Western blotting as compared to expression of NRF2 alone. Delivery of NRF2 loaded-EVs using this strategy leads to induction of target gene expression in a HEK cell assay. Generating polypeptide construct based on other EV proteins also resulted in similar effect, for instance when using Alix and syntenin. FIG. 13 shows a similar experiment as in FIG. 5, but here with a cis-cleaving intein (comprising the amino acid sequence Val-Val-Val-His-Asn (SEQ ID NO: 1)) as a release system fused to CD63, CD81 (data not shown), and syntenin (data not shown) and to Cas9, and delivered using amino epithelial cells. As can be seen from FIG. 13, only the unmutated intein induced relevant levels of NHEJ.

Another example of the NLS-NLSBP polypeptide-based endogenously activated release system includes the fusion of KPNA2 to exosomal protein CD47 and co-expressing it with the transcription factor HSF1 in fibroblasts, thus loading HSF1 into exosomes. The fibroblast-derived exosomes were isolated and used to treat mouse primary cerebellar granule neurons that had been subjected to low or high potassium concentration in their culture media. HSF1-loaded EV treatment led to significantly higher cell viability compared to the treatment with control exosomes without the NLS-NLSBP release system at apoptosis-inducing low potassium conditions.

The invention claimed is:

1. An extracellular vesicle (EV) comprising at least one polypeptide construct comprising:
   (i) at least one polypeptide of interest (PoI);
   (ii) at least one exosomal polypeptide; and,
   (iii) a monomeric cis-cleaving intein,
   wherein the monomeric cis-cleaving intein releases the at least one PoI from the at least one exosomal polypeptide into the lumen of the EV upon activation within the EV, and
   wherein the at least one PoI is unconjugated upon release.

2. The EV according to claim 1, wherein the PoI is a therapeutic polypeptide selected from the group consisting of antibodies, intrabodies, single chain variable fragments, affibodies, enzymes, tumor suppressors, viral or bacterial inhibitors, cell component proteins, deoxyribonucleic acid (DNA) and/or ribonucleic acid (RNA) binding proteins, DNA repair inhibitors, nucleases, proteinases, integrases, transcription factors, growth factors, apoptosis inhibitors and inducers, toxins, structural proteins, neurotrophic factors, membrane transporters, nucleotide binding proteins, heat shock proteins, clustered regularly interspaced short palindromic repeats (CRISPR)-associated proteins, and any combination thereof.

3. The EV of claim 2, wherein the PoI is an enzyme for enzyme replacement therapy or gene editing.

4. The EV according to claim 1, wherein the exosomal polypeptide is selected from the group consisting of cluster of differentiation 9 (CD9), cluster of differentiation 53(CD53), cluster of differentiation 63 (CD63), cluster of differentiation 81 (CD81), cluster of differentiation 54 (CD54), cluster of differentiation 50 (CD50), flotillin 1(FLOT1), flotillin 2 (FLOT2), cluster of differentiation 49d (CD49d), cluster of differentiation 71 (CD71), cluster of differentiation 133 (CD133), cluster of differentiation 138 (CD138), cluster of differentiation 235a (CD235a), apoptosis-linked gene-2 interacting protein X (ALIX), syntenin-1, syntenin-2, lysosome-associated membrane protein 2b (lamp2b), tetraspanin-8 (TSPAN8), tetraspanin-14 (TSPAN14), cluster of differentiation 37 (CD37), cluster of differentiation 82 (CD82), cluster of differentiation 151 (CD151), cluster of differentiation 231 (CD231), cluster of differentiation 102 (CD102), notch homolog 1, translocation-associated (NOTCH1), neurogenic locus notch homolog protein 2 (NOTCH2), neurogenic locus notch homolog protein 3 (NOTCH3), neurogenic locus notch homolog 4 (NOTCH4), delta-like protein 1 (DLL1), delta-like protein 4(DLL4), jagged 1 protein (JAG1), jagged 2 protein (JAG2), CD49d/Integrin Subunit Alpha 4 (ITGA4), Integrin Subunit Beta 5 (ITGB5), Integrin Subunit Beta 6 (ITGB6), Integrin Subunit Beta 7 (ITGB7), cluster of differentiation 11a (CD11a), cluster of differentiation 11b (CD11b), cluster of differentiation 11c (CD11c), cluster of differentiation 18 (CD18)/Integrin Subunit Beta 2 (ITGB2), cluster of differentiation 41 (CD41), cluster of differentiation 49b (CD49b), cluster of differentiation 49c (CD49c), cluster of differentiation 49e (CD49e), cluster of differentiation 51 (CD51), cluster of differentiation 61 (CD61), cluster of differentiation 104 (CD104), tetraspanins, Fc receptors, interleukin receptors, immunoglobulins, major histocompatibility complex (MHC)-I or MHC-II components, cluster of differentiation 2 (CD2), cluster of differentiation 3 (CD3) epsilon, CD3 zeta, cluster of differentiation 13 (CD13), cluster of differentiation 18 (CD18), cluster of differentiation 19 (CD19), cluster of differentiation 30 (CD30), cluster of differentiation 34 (CD34), cluster of differentiation 36 (CD36), cluster of differentiation 40 (CD40), CD40L, cluster of differentiation 44 (CD44), cluster of differentiation 45 (CD45), CD45RA, cluster of differentiation 47 (CD47), cluster of differentiation 86 (CD86), cluster of differentiation 110 (CD110), cluster of differentiation (CD111), cluster of differentiation 115 (CD115), cluster of differentiation 117 (CD117), cluster of differentiation 125 (CD125), cluster of differentiation 135 (CD135), cluster of differentiation 184 (CD184), cluster of differentiation 200 (CD200), cluster of differentiation 279 (CD279), cluster of differentiation 273 (CD273), cluster of differentiation 274 (CD274), cluster of differentiation 362 (CD362), Collagen Type VI Alpha 1 Chain (COL6A1), Agrin (AGRN), epidermal growth factor receptor (EGFR), Glyceraldehyde-3-Phosphate Dehydrogenase (GAPDH), glutamate receptor 2 (GLUR2), glutamate receptor 3 (GLUR3), human leukocyte antigen DM (HLA-DM), heparan sulfate proteoglycan 2 (HSPG2), L1 cell adhesion molecule (L1CAM), laminin subunit beta-1 (LAMB1), laminin subunit gamma-1 (LAMC1), lymphocyte function-associated antigen 1 (LFA-1), lectin galactoside-binding soluble 3 binding protein (LGALS3BP), macrophage-1 (Mac-1) alpha, Mac-1 beta, milk fat globule epidermal growth factor 8 (MFGE8), slit homolog 2 protein (SLIT2), syntaxin 3 (STX3), T-cell receptor alpha (TCRA), T-cell receptor beta (TCRB), T-cell receptor delta (TCRD), T-cell receptor gamma (TCRG), vesicle transport through interaction with t-soluble NSF attachment receptors homolog 1A (VTI1A), and vesicle transport through interaction with t-soluble NSF attachment receptors homolog 1B (VTI1B).

5. The EV according to claim 1, wherein the EV further comprises at least one polynucleotide of interest.

6. The EV according to claim 1, wherein the EV further comprises at least one targeting moiety.

7. The EV according to claim 1, wherein the release of the at least one PoI is triggered by a change in pH.

8. The EV according to claim 1, wherein the monomeric cis-cleaving intein is a slow-cleaving intein.

9. The EV according to claim 1, wherein the monomeric cis-cleaving intein comprises the sequence Val-Val-Val-His-Asn (SEQ ID NO: 1).

10. The EV according to claim 1, wherein the monomeric cis-cleaving intein comprises the sequence Val-Val-Val-His-Asn-Cys (SEQ ID NO: 2).

11. A cell comprising at least one EV according to claim 1.

12. A pharmaceutical composition comprising at least one EV according to claim 1.

* * * * *